(12) United States Patent
Wilkhu et al.

(10) Patent No.: US 11,160,757 B1
(45) Date of Patent: Nov. 2, 2021

(54) PH DEPENDENT RELEASE COATED MICROPARTICLE CANNABINOID FORMULATIONS

(71) Applicant: GW Research Limited, Cambridge (GB)

(72) Inventors: Jitinder Wilkhu, Cambridge (GB); Alan Silcock, Cambridge (GB)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 17/068,326

(22) Filed: Oct. 12, 2020

(51) Int. Cl.
| | |
|---|---|
| *A61K 9/16* | (2006.01) |
| *A61K 31/352* | (2006.01) |
| *A61K 31/05* | (2006.01) |
| *A61K 9/08* | (2006.01) |
| *A61K 9/10* | (2006.01) |
| *A61K 9/48* | (2006.01) |
| *A61K 9/20* | (2006.01) |

(52) U.S. Cl.
CPC .............. *A61K 9/1652* (2013.01); *A61K 9/08* (2013.01); *A61K 9/10* (2013.01); *A61K 9/1617* (2013.01); *A61K 9/1635* (2013.01); *A61K 9/2013* (2013.01); *A61K 9/2054* (2013.01); *A61K 9/4808* (2013.01); *A61K 9/4858* (2013.01); *A61K 9/4866* (2013.01); *A61K 31/05* (2013.01); *A61K 31/352* (2013.01)

(58) Field of Classification Search
CPC .... A61K 9/1652; A61K 9/1635; A61K 31/05; A61K 9/08; A61K 9/1617; A61K 9/4858; A61K 9/2054; A61K 9/4808; A61K 9/2013; A61K 31/352; A61K 9/10; A61K 9/4866

See application file for complete search history.

(56) References Cited

U.S. PATENT DOCUMENTS

| | | |
|---|---|---|
| 6,403,126 B1 | 6/2002 | Webster |
| 6,949,582 B1 | 9/2005 | Wallace |
| 8,293,786 B2 | 10/2012 | Stinchcomb |
| 8,673,368 B2 | 3/2014 | Guy et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |

(Continued)

FOREIGN PATENT DOCUMENTS

| | | |
|---|---|---|
| CA | 2 737 447 A1 | 10/2012 |
| CA | 2 859 934 A1 | 3/2016 |

(Continued)

OTHER PUBLICATIONS

U.S. Appl. No. 15/640,033, filed Jun. 30, 2017.

(Continued)

*Primary Examiner* — Carlos A Azpuru
(74) *Attorney, Agent, or Firm* — Cooley LLP

(57) ABSTRACT

The present disclosure provides a microparticulate comprising one or more cannabinoids and a pH dependent release polymer. In embodiments, the one or more cannabinoids are present in an amount ranging from 10% w/w to about 50% w/w. In embodiments, the pH dependent release polymer is present in an amount ranging from ranging from about 5% w/w to about 85% w/w.

30 Claims, 1 Drawing Sheet

Graph depicting the area under the curve (AUC) for the 7-COOH CBD metabolite from the bioavailability study

(56) References Cited

U.S. PATENT DOCUMENTS

| | | |
|---|---|---|
| 9,259,449 B2 | 2/2016 | Raderman |
| 9,474,726 B2 | 10/2016 | Guy et al. |
| 9,522,123 B2 | 12/2016 | Whalley et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,092,525 B2 | 10/2018 | Guy et al. |
| 10,111,840 B2 | 10/2018 | Guy et al. |
| 10,137,095 B2 | 11/2018 | Guy et al. |
| 2004/0049059 A1 | 3/2004 | Muller |
| 2004/0110828 A1 | 6/2004 | Chowdhury et al. |
| 2005/0042172 A1 | 2/2005 | Whittle |
| 2005/0266108 A1 | 12/2005 | Flockhart et al. |
| 2006/0039959 A1 | 2/2006 | Wessling |
| 2007/0060638 A1 | 3/2007 | Olmstead |
| 2007/0060639 A1 | 3/2007 | Wermeling |
| 2008/0119544 A1 | 5/2008 | Guy et al. |
| 2008/0188461 A1 | 8/2008 | Guan |
| 2009/0035368 A1 | 2/2009 | Moschwitzer |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0231083 A1 | 9/2012 | Carley et al. |
| 2012/0270845 A1 | 10/2012 | Bannister |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0110828 A1 | 4/2014 | Otremba et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Guy et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0167583 A1 | 6/2019 | Shah et al. |
| 2019/0175547 A1 | 6/2019 | Stott et al. |
| 2019/0314296 A1 | 10/2019 | Wright et al. |

FOREIGN PATENT DOCUMENTS

| | | |
|---|---|---|
| CN | 101040855 A | 9/2007 |
| CN | 103110582 A | 5/2013 |
| DE | 10 2012 105 063 A1 | 12/2013 |
| GB | 2384707 A | 8/2003 |
| GB | 2434097 A | 7/2007 |
| GB | 2434312 A | 7/2007 |
| GB | 2438682 A | 12/2007 |
| GB | 2450753 A | 1/2009 |
| GB | 2456183 A | 7/2009 |
| GB | 2471523 A | 1/2011 |
| GB | 2471565 A | 1/2011 |
| GB | 2478595 A | 9/2011 |
| GB | 2479153 A | 10/2011 |
| GB | 2487712 A | 8/2012 |
| GB | 2478072 B | 12/2012 |
| GB | 2478074 B | 12/2012 |
| GB | 2492487 A | 1/2013 |
| GB | 2531282 A | 4/2016 |
| WO | WO 2002/064109 A2 | 8/2002 |
| WO | WO 2003/099302 A1 | 12/2003 |
| WO | WO 2004/016246 A1 | 2/2004 |
| WO | WO 2004/016277 A2 | 2/2004 |
| WO | WO 2006/054057 A2 | 5/2006 |
| WO | WO 2006/133941 A2 | 12/2006 |
| WO | WO 2007/032962 A2 | 3/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/021394 A2 | 2/2008 |
| WO | WO 2008/024490 A | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 2/2009 |
| WO | WO 2010/012506 A1 | 2/2010 |
| WO | WO 2011/001169 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/032351 A1 | 3/2013 |
| WO | WO 2014/146699 A1 | 9/2014 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/059405 A1 | 4/2016 |
| WO | WO 2016/084075 A1 | 6/2016 |
| WO | WO 2016/118391 A1 | 7/2016 |
| WO | WO 2016/147186 A1 | 9/2016 |
| WO | WO 2016/022936 A1 | 11/2016 |
| WO | WO 2016/199148 A1 | 12/2016 |
| WO | WO 2017/168138 A1 | 10/2017 |
| WO | WO 2018/002636 A1 | 1/2018 |
| WO | WO 2018/002637 A1 | 1/2018 |
| WO | WO 2018/035030 A1 | 2/2018 |
| WO | WO 2018/037203 A1 | 3/2018 |
| WO | 2019082171 A1 * | 5/2019 |
| WO | WO 2019/082171 A1 | 5/2019 |
| WO | WO 2019/159174 A1 | 8/2019 |
| WO | WO 2020/240184 A1 | 12/2020 |

OTHER PUBLICATIONS

U.S. Appl. No. 16/314,583, filed Dec. 31, 2018.
U.S. Appl. No. 16/314,569, filed Dec. 31, 2018.
[No Author Listed], "Cannabidiol Therapy for Aicardi Syndrome" Aug. 2014, 4 pages.
[No Author Listed], Cover and Table of Contents, J Pharmacology and Exp Therapeutics, Feb. 2010, 332(2), 4 pages.

(56) References Cited

OTHER PUBLICATIONS

[No Author Listed], "Missouri House passes cannabis extract legislation," Kansas City Star, 2014, https://kansascity.com/news/politics-government/article346747.html, 2 pages.

Alger, "Not too excited? Thank your endocannabinoids," Neuron, 51(4):393-595 (2006).

American Epilepsy Society, "Three Studies Shed New Light on the Effectiveness of Cannabis in Epilepsy," Oct. 14, 2014, 2 pages.

Ames et al., "Anticonvulsant effect of cannabidiol," S Afr Med J. Jan. 4, 1986; 69(1):14, 1 page.

Appendino, J. P. et al., "Position Statement on the Use of Medical Cannabis for the Treatment of Epilepsy in Canada," Can J. Neurol. Sci., 33:783-786 (2006).

Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019].

Arain, "Pregabalin in the management of partial epilepsy," Neuropsychiatr Dis Treat., 407-13 (2009); Epub Aug. 20, 2009.

Arimanoglou et al., "All children who experience epileptic falls do not necessarily have Lennox-Gastaut syndrome . . . but many do," Epileptic Discord, 13:S3-S13 (2011).

Arslan, A. & Tirnaksiz, F., "Self-emulsifying Drug Delivery Systems," F ABAD J Pharm Sci, 38(1):55-64 (2013).

Avoli et al. "Cellular and molecular mechanisms of epilepsy in the human brain," Prog Neurobiol., 77(3):166-200 (2005).

Bakhsh, "Pregabalin in the management of partial epilepsy," Miftaah-al-Khazaain, 1930:607-608, with English translation, 4 pages.

Bancaud, "Proposal for Revised Clinical and Electroencephalographic Classification of Epileptic Seizures," Epilepsia, 22(4):489-501 (1981).

Banerjee et al., "Case Report: Aicardi syndrome: A report of five Indian cases," Neurology India, 54(1):91-93 (2006).

Barker-Haliski et al. "How Clinical Development Can, and Should Inform Translational Science," Neuron, 84:582-593 (2014).

Benowitz et al. "Metabolic and Psychophysiologic studies of cannabidiol hexobarbital interaction," Clin Pharmacal Ther., 28(1):115-120 (1980).

Benowitz & Jones, "Cardiovascular and metabolic considerations in prolonged cannabinoid administration in man," J Clin Pharm, 21:214S-223S (1981).

Bertram, "The Relevance of Kindling for Human Epilepsy," Epilepsia, 48(Suppl. 2):65-74 (2007).

Bhatt, V. P. & Vashishtha, D. P., "Indigenous plants in traditional healthcare system in Kedarnath valley of western Himalaya," Indian J Tradit Knowl., 7(2):300-310 (2000).

Bhattacharyya, et al. "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi:10.1001/archgenpsychiatry.2009 .17.

Bipolar Health Group (Charlotte's Web Hemp Remedy, available online at http:/bipolarhealthgroup.org/index.php/charlottes-web-hemp-remedy/, accessed Sep. 6, 2017, 6 pages.

cdc.gov [online], "2 to 20 years: girls Stature-for-age and Weigh-for-age percentiles," National Center for Health Statistics and National Center for Chronic Disease Prevention and Health Promotion, last modified Nov. 2000, <https://www.cdc.gov/growthcharts/data/set1clinical/cj4aa022.pdf>, 1 page.

Booth, "Legalization's opening of medical pot research is dream and nightmare," Denver Post, Dec. 14, 2013, 6 pages.

Bostanci, M. O. & Bagirici, F., "The effects of octanol on penicillin induced epileptiform activity in rats: an in vivo study," Epilepsy Research, 71:188-194 (2006).

Braida, et al., "Post-ischemic treatment with cannabidiol prevents electroencephalographic flattening, hyperlocomotion and neuronal injury in gerbils," Neuroscience Letters., 346:61-64 (2003).

Brust, J. C. M. et al., "Marijuana use and the risk of new onset seizures," Trans Am Clin Climatol Assoc., 103:176-181 (1992).

Carlini et al., "Hypnotic and antiepileptic effects of cannabidiol," J Clin Pharmacol., 21:417S-427S (1981).

Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.

Charlotte's Web [online], "When to expect Results from CW Hemp Oil," Mar. 13, 2017, retrieved on May 21, 2018, URL https://www.cwhemp.com/blog/expecting-results-from-hemp, 6 pages.

Charlotte's Web [online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.

ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/lgs-Lennox-gastaut-syndrome, 10 pages.

Chiron, C. & Dulac, O., "The Pharmacologic Treatment of Dravet Syndrome," Epilepsia, 52 (Suppl. 2):72-75 (2011).

Chiu, P. et al., "The Influence of Cannabidiol and Δ-Tetrahydrocannabinol on Cobalt Epilepsy in Rats," Epilepsia, 20:365-375 (1979).

Chou, "Theoretical basis, experimental design, and computerized simulation of synergism and antagonism in drug combination studies," Pharmacol Rev., 58(3):621-681 (2006).

Conry et al., "Clobazam in the treatment of Lennox-Gastaut syndrome," Epilepsia, 50:1158-1166 (2009).

Consroe et al. Chapter 12, "Potential Role of Cannabinoids for Therapy of Neurological Disorders," in Marijuana Cannabinoids: Neurobiology and Neurophysiology, Ed. L. Murphy (1992), 72 pages.

Consroe et al. "Anticonvulsant drug antagonism of delta9tetrahydrocannabinol-induced seizures in rabbits," Res Commun Chem Pathol Pharmacol., 16(1):1-13 (1977).

Consroe et al. "Anticonvulsant interaction of cannabidiol and ethosuximide in rats," J Pharm Pharmacol., 29(8):500-501 (1977). doi:10.1111/j.2042-7158.1977.tb11378.x.

Consroe et al. "Anticonvulsant nature of marihuana smoking," JAMA, 234(3):306-307 (1975).

Consroe, P. & Wolkin, A., "Cannabidiol—antiepileptic drug comparisons and interactions in experimentally induced seizures in rats," J Pharmacol Exp Ther. Apr. 1977;201(1):26-32.

Consroe et al. "Effects of cannabidiol on behavioral seizures caused by convulsant drugs or current in mice," Eur J Pharmacol., 83(3-4):293-298 (1982).

Consroe, P. & Snider, S. R., "Chapter 2. Therapeutic Potential of Cannabinoids in Neurological disorders," Cannabinoids as Therapeutic Agents, R. Mechoulam, Ed., pp. 21-49 (1986).

Consroe et al., "Controlled clinical trial of cannabidiol in Huntington's Disease," Pharmacology Biochemistry & Behavior, 40:701-708 (1991).

Cortesi et al. "Potential therapeutical effects of cannabidiol in children with pharmacoresistant epilepsy," Med Hypotheses, 68(4):920-921 2007). Epub Nov. 16, 2006.

Cortez & Snead, "Chapter 10: Pharmacologic Models of Generalized Absence Seizures in Rodents," Models of Seizures and Epilepsy, 111-126 (2006).

Cunha et al. "Chronic administration of cannabidiol to healthy volunteers and epileptic patients." Pharmacology, 21(3):175-85 (1980).

Curia et al., "The pilocarpine model of temporal lobe epilepsy," J Neuroscience Methods, 172(2-4):143-157 (2008).

Czapinski, et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci., 150:S162 (1997).

Dasa et al. "Key Attributes of TKDL: Ganja," Brhat Nighantu Ratnakara (Saligramanighantubhusanam), RS/4336, vol. IV. 1997:170, with English translation, 5 pages.

Davis et al. "Antiepileptic action of marijuana-active substances," Federation Proceedings, 8:284-285 (1949).

(56) References Cited

OTHER PUBLICATIONS

Davis et al. "A predominant role for inhibition of the adenylate cyclase/protein kinase A pathway in ERK activation by cannabinoid receptor 1 in NIE-115 neuroblastoma cells." J Biol Chem. 278(49):48973-80 (2003). Epub Sep. 29, 2003.
De Meijer, "Chapter 5: The Chemical Phenotypes (Chemotypes) of Cannabis," Handbook of Cannabis, Ed. Roger G. Pertwee, pp. 89-110 (2014).
De Oliveira, et al. "Anticonvulsant activity of β-caryophyllene against pentylenetetrazol-induced seizures." Epilepsy Behav., 56:26-31 (2016). doi: 10.1016/j.yebeh.2015.12.040.
Deshpande, et al. "Cannabinoid CB 1 receptor antagonists cause status epilepticus-like activity in the hippocampal neuronal culture model of acquired epilepsy." Neurosci Lett., 41 I(I):1-6 (2007). Epub Nov. 15, 2006.
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edukesearch-education/cannabidiol-conference>.
Dravet, "The core Dravet syndrome phenotype," Epilepsia. 52 Suppl 2:3-9. doi: 10.1111/j.1528-1167.2011.02994.x. (2011).
Dreifus et al., "Proposal for Revised Clinical and Electroencephalographic Classification of Epileptic Seizures," Epilepsie, 22:489-501 (1981).
Dulac, "Use of Lamotrigine in Lennox-Gastaut and Related Epilepsy Syndromes," J. Child Neurolog., 12(Supplement 1), S23-S29 (1997).
Dulac, "Vigabatrin in Childhood Epilepsy," J. Child Neurolog., 6(Supplement 2), S30-S37 (1991).
Eadie, "Shortcomings in the current treatment of epilepsy," Expert Rev Neurother, 12(12):1419-27 (2012).
Eggers, "'Temporal lobe epilepsy is a disease of faulty neuronal resonators rather than oscillators, and all seizures are provoked, usually by stress," Med Hypotheses., 69(6):1284-9 (2007).
Elsohly and Gul. "Constituents of Cannabis Sariva," Chapter 1, Handbook of Cannabis, ed. Roger G. Pertwee, pp. 3-22 (2014).
Engel. "Report of the ILAE classification core group." Epilepsia. Sep. 2006;47(9): 1558-68.
Engel, "Chapter 1: What Should be Modeled?" In Models Seizure Epilepsy, 2006, 14 pages.
Fariello. "Parenteral Penicillin in Rats: An Experimental Model of Multifocal Epilepsy," Epilepsia, 17:217-222 (1976).
FDA [online]. "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online]. "Warning Letters and Test Results for Cannabidiol-Related Products," 2016 Warning Letters, retrieved on Nov. 14, 2017, URL <https://www.fda.gov/newsevents/publichealthfocus/ucm484109.htm>, 4 pages.
Ferdinand, et al., "Cannabis—psychosis pathway independent of other types of psychopathology," Schizophr Res., 79(2-3):289-295 (2005).
Fisher et al., "The impact of epilepsy from the patient's perspective I. Descriptions and subjective perceptions," Epilepsy Res. Aug. 2000;41(1):39-51.
Gabor et al. "Lorazepam versus phenobarbital • Candidates for drug of choice for treatment of status epilepticus," J Epilepsy. Jan. 1990;3(1):3-6.
Gallily, et al., "Overcoming the Bell-Shaped Dose-Response of Cannabidiol by Using Cannabis Extract Enriched in Cannabidiol," Pharmacology & Pharmacy, 6:75 (Jan. 2015).
Gardner [online], "Comes Now Epidiolex (FDA Approves IND Studies of CBD)," BeyondTHC.com, Oct. 22, 2013, retrieved on Jan. 31, 2018, URL http://www.beyondthc.com/comes-now-epidiolex-fda-approves-ind-studies-of-cbd, 4 pages.
Gastaut, "Clinical and electroencephalographical classification of epileptic seizures" Epilepsia, Mar. 1970;II(I):102-13.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Green, "CBD: An Unconventional Therapy," available online at http://nugs.com/article/cbd-an unconventional-therapy.html, published Mar. 24, 2014, 5 pages.
Geffrey et al. "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Gresham et al "Treating Lennox-Gastaut syndrome in epileptic pediatric patients with third generation rufinamide," Neuropsychiatr Dis Treat., 6:639-645, Oct. 5, 2010.
Gross et al. "Marijuana use and epilepsy: prevalence in patients of a tertiary care epilepsy center," Neurology, Jun. 8, 2004; 62(11 ):2095-7.
Grotenhermen, "Epilepsiebehandlung des Angelman-Syndromes mit CBD (Cannabidiol) (Epilepsy treatment of Angelman syndrome with CBD (cannabidiol)," Angelman e. V., Jan. 2015, retrieved on Jun. 7, 2019, URL <http://s8a5e4d6fcfb04b6.jimcontent.com/download/Version/1472724876/module//9873059694/name/Epilepsiebehandlung%2Odurch%20CBD.pdf> (with Machine English translation), 8 pages.
Guerrini et al., "Lamotrigine and Seizure Aggravation in Severe Myoclonic Epilepsy," Epilepsia, 39(5):508-512, 1998.
Guimaraes, et al. "Antianxiety effect of cannabidiol in the elevated plus-maze," Psychopharmacology (Berl). 1990;100(4):558-9. doi: 10.1007/BF02244012.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.

(56) References Cited

OTHER PUBLICATIONS

Heinemann et al., "An Overview of in Vitro Seizure Models in Acute and Organotypic Slices," Chapter 4, 35-44 (2006).
Hill et al. "Δ9-Tetrahydrocannabivarin suppresses in vitro epileptiform and in vivo seizure activity in adult rats." Epilepsia. Aug. 2010;51(8):1522-32. doi: 10.1111/j.1528-1167.2010.02523.x. Epub Feb. 26, 2010.
Hill, "Cannabidivarin-rich cannabis extracts are anticonvulsant in mouse and rat via a CB 1 receptor-independent mechanism," British Journal of Pharmacology, Oct. 2013, 170(3): 679-692.
Hill et al., "Cannabidivarin is anticonvulsant in mouse and rat," Br J Pharmacal, 167(8):1629-1642 (2012).
Holmes et al., "Choosing the correct AED: From Animal Studies to the Clinic," Pediatr Neurol. Mar. 2008; 38(3): 151-162.
Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability."ACS Chem Neurosci. Nov. 19, 2014;5(11):1131-41. doi: 10.1021/cn5000524.
ICE Epilepsy Alliance, the Dravet Syndrome Spectrum, Nov. 2, 2008, 2 pages.
IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.
Iuvone et al., "Neuroprotective effect of cannabidiol, a non-psychoactive component from Cannabis sativa, on beta-amyloid-induced toxicity in PC12 cells." J Neurochem. Apr. 2004;89(1 ): 134-41.
Izzo et al., "Non-psychotropic plant cannabinoids: new therapeutic opportunities from an ancient herb." Trends in Pharmacological Sciences. 30(10): 515-527, 2009.
Jacobson, "Survey of Current Cannabidiol Use in Pediatric Treatment-Resistant Epilepsy," Apr. 22, 2013.
Jeavons et al., "Sodium valproate in treatment of epilepsy." Br Med J. Jun. 15, 1974,2(5919):584-6.
Jones et al. [online], Info & Metrics / Article Information, "Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exp Ther., 332(2):559-577 (2010).
Joy, et al. "Marijuana and Medicine. Assessing the Science Base." National Academy Press. Washington D.C. 1999. 170 pages.
Kahan, et al. "Risk of selection bias in randomized trials," Trials, 16:405 (2015), 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al. "The cannabinoids as potential antiepileptics," J Clin Pharmacol, 21(8-9 Suppl):437S-447S (1981).
Karler et al., "The anticonvulsant activity of cannabidiol and cannabinol," Life Science, 13:1527-1531 (1973).
Kelley, et al. "Doose syndrome (myoclonic-astatic epilepsy): 40 years of progress," Developmental Medicine & Child Neurology, Aug. 2010, 52: 988-993.
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.

Khan et al., "Key Attributes of TKDL: Zimad-e-qinnab," Khazaain-al-Adiva, 1911 (with English translation), 5 pages.
Kuhn et al., "Potent activity of carfilzomib, a novel, irreversible inhibitor of the ubiquitin-proteasome pathway, against preclinical models of multiple myeloma," Blood, 110(9):3281-3290 (2007).
Klitgaard et al., "Electrophysiological, neurochemical and regional effects of levetiracetam in the rat pilocarpine model of temporal lobe epilepsy," Seizure., 12(2):92-100, Mar. 2003.
Klitgaard et al., "Evidence for a unique profile of levetiracetam in rodent models of seizures and epilepsy." European journal of pharmacology. Jul. 24, 1998, 353(2): 191-206.
Kramer et al., "Febrile infection-related epilepsy syndrome (FIRES): pathogenesis, treatment, and outcome: a multicenter study on 77 children." Epilepsia. Nov. 2011;52(11): 1956-65. doi:10.1111/j.1528-1167.2011.03250.x. Epub Aug. 29, 2011.
Kruk-Slomka et al., "A comparison of mecamylamine and bupropion effects on memory-related responses induced by nicotine and scopolamine in the novel object recognition test in mice," Pharmacological Reports, 66(4):638-646 (2014).
Kurz & Blass, "Use of dronabinol (delta-9-THC) in autism: A prospective single-case-study with an early infantile autistic child," Cannabinoids, 5(4):4-6 (2010).
Kwan et al., "Definition of drug resistant epilepsy: consensus proposal by the ad hoc Task Force of the ILAE Commission on Therapeutic Strategies," Epilepsia. Jun. 2010,51(6):1069-77. doi:10.1111/j.1528-1167.2009.02397.x. Epub Nov. 3, 2009. Erratum in: Epilepsia. Sep. 2010,51(9): 1922.
LaPrarie et al., "Cannabidiol is a negative allosteric modulator of the cannabinoid CB1 receptor," British J Pharmacology, 172(20):4790-4805 (2015).
LeafScience.com [online], "What are the Highest CBD Strains?" Oct. 15, 2014, retrieved on Feb. 16, 2017, URL www.leafscience.com/2014/10/15/highest-cbd-strains/, 2 pages.
Leo et al., "Cannabidiol and epilepsy: Rationale and therapeutic potential," Pharmacological Research, 107:85-92 (2016).
Lewis, "Mystery Mechanisms," the Scientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al. "Assessment of self-selection bias in a pediatric unilateral hearing loss study," Otolarvnzol Head Neck Surz. 142(3): 427-433 (2010).
Lindamood and Colasanti, Effects of delta 9-tetrahydrocannabinol and cannabidiol on sodium-dependent high affinity choline uptake in the rat hippocampus. J Pharmacology Experimental Therapeutics, 1980, 213(2):216-221.
Long et al., "The pharmacological actions of cannabidiol," Drugs of the Future. Jul. 2005;30(7):747-53.
Loscher and Schmidt, "Modern antiepileptic drug development has failed to deliver: ways out of the current dilemma." Epilepsia. Apr. 2011;52(4):657-78. doi: 10.1111/j.1528-1167.2011.03024.x.
Lowenstein, "Chapter 363: Seizures and Epilepsy," Diseases of the Central Nervous System, 2008, 2498-2512.
Luttjohann et al. "A revised Racine's scale for PTZ-induced seizures in rats." Physiol Behav. Dec. 7, 2009;98(5):579-86. doi: 10.1016/j.physbeh.2009.09.005.
Lutz, "On-demand activation of the endocannabinoid system in the control of neuronal excitability and epileptiform seizures." Biochem Pharmacol. Nov. 1, 2004;68(9):1691-8.
Maa et al., "The case for medical marijuana in epilepsy," Epilepsia. Jun. 2014;55(6):783-6. doi: 10.1111/epi.12610.
Mackie, "Cannabinoid receptors as therapeutic targets," Annu Rev Pharmacol Toxicol. 2006;46: 101-22.
Majoosi et al., "Key Attributes of TKDL: Saoot Baraae Sara," Kaamil-al-Sena'ah, Central Council for Research in Unani Medicine, 2005 (with English translation), 2 pages.
Malfait et al., "The nonpsychoactive cannabis constituent cannabidiol is an oral anti-arthritic therapeutic in murine collagen-induced arthritis," PNAS, Aug. 15, 2000, 97(17):9561-9566.
Manni et al., "Obstructive Sleep Apnea in a Clinical Series of Adult Epilepsy Patients: Frequency and Features of the Comorbidity," Epilepsia, 44(6):836-840 (2003).
Manno, "Status Epilepticus: Current Treatment Strategies," The Neurohospitalist. Jan. 2011, 1(1):23-31.

(56) References Cited

OTHER PUBLICATIONS

Mares et al., "Electrical Stimulation-Induced Models of Seizures in Model of Seizures and Epilepsy Asla Pitkanen," Philip A. Schwartzkroin & Solomon L. Moshe (Eds.), pp. 153-159 (2004).
Martin et al., "Structure-Anticonvulsant Activity Relationships of Cannabidiol Analogs," National Institute on Drug Abuse, Research Monograph Series, 1987, 79:48-58. Marinol Label Retrieved from: https://www.accessdata.fda.gov/dmgsatfda docs/label/2006/018651 502550261b1. pdf.
Mattson et al., "Comparison of carbamazepine, phenobarbital, phenytoin, and primidone in partial and secondarily generalized tonic-clonic seizures," N. Engl. J. Med, 313(3): 145-151, Jul. 18, 1985.
Mattson et al., "Prognosis for total control of complex partial and secondary generalized tonic clonic seizures," Neurology, 47:68-76, 1996.
McCormick et al., "On the cellular and network bases of epileptic seizures," Annu Rev Physiol. 2001;63:815-46.
McNamara, "Chapter 19: Pharmacotherapy of the Epilepsies," Goodman & Gilman's The Pharmacological Basis of Therapeutics 11th ed., McGraw-Hill Companies, pp. 501-525 (2006).
Mechoulam et al., "Cannabidiol: An Overview of Some Pharmacological Aspects," J Clin Pharmacol, 2002, 42:11S-19S.
Mechoulam et al., "Toward drugs derived from cannabis," Naturwissenschaften. Apr. 1978;65(4): 174-9.
Medicos [online]. "Convulsive Disorders and their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving>, 3 pages.
Merlis, "Proposal for an International Classification of the Epilepsies," Epilepsia, 11:114-119 (1970).
Miller et al., "Mapping genetic modifiers of survival in a mouse model of Dravet syndrome," Genes, Brain and Behavior, 13:163-172 (2014).
Moral et al., "Pipeline on the Move," Drugs of the Future, Jan. 2014, 39(1): 49-56.
Morard et al., "Conversion to Sirolimus-Based Immunosuppression in Maintenance Liver Transplantation Patients," Liver Transplantation, 13:658-664, 2007.
Morelli et al., "The effects of cannabidiol and its synergism with bortezomib in multiple myeloma cell lines. A role for transient receptor potential Vanilloid type-2," Int J Cancer, 134(11):2534-2546 (2014).
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabissi et al., "Cannabinoids synergize with cafilzomib, reducing multiple myeloma cells viability and migration," Oncotarget, 7:77553 (2016).
Neto et al., "The role of polar phytocomplexes on anticonvulsant effects of leaf extracts of Lippia Alba (Mill.) N.E. Brown chemotypes," J. Pharm Pharmacol. 61(7):933-9 (2009).
Ng et al., "Illicit drug use and the risk of new-onset seizures." Am J Epidemiol. Jul. 1990; 132(1):47-57.
Oakley et al., "DRAVET Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazole-induced seizures in rats," Peptides. Jun. 2007;28(6): 1214-9. Epub Apr. 19, 2007.
Pelliccia et al., [Online], "Treatment with CBD in oily solution of drug-resistant pediatric epilepsies," 2005 Congress on Cannabis and the Cannabinoids, Leiden, The Netherlands: International Association for Cannabis as Medicine, 2005, 14, retrieved on Jun. 30, 2015, URL <http//www.cannabis-med.org/studies/ww_en_db_study_show.php?s_id=173&&search_pattern=EPILEPSY>, 2 pages, Abstract only.
Pereira et al., "Study pharmacologic of the GABAergic and glutamatergic drugs on seizures and status epilepticus induced by pilocarpine in adult Wistar rats," Neurosci Lett. Jun. 4, 2007;419(3):253-7. Epub Apr. 13, 2007.
Pertwee, "Cannabinoid receptor ligands: clinical and neuropharmacological considerations, relevant to future drug discovery and development," Expert Opin Investig Drugs. Jul. 2000;9(7): 1553-71.
Pertwee, "Chapter 3: The Pharmacology and Therapeutic Potential of Cannabidiol," Cannabinoids, Ed Vincenzo Di Marzo ed., 2004, 32-83.
Pertwee, "The diverse CB1 and CB2 receptors pharmacology of three plant cannabinoids: Alpha9 Tetrahydrocannabinol, cannabidiol and alpha9-tetrahydrocannabivarin," Br. J. Pharmacol. 153 (2): 199-215, 2008.
Petrocellis, et al., "Effects of cannabinoids and cannabinoid-enriched Cannabis extracts on TRP channels and endocannabinoid metabolic enzymes," British Journal of Pharmacology (2011) 1631479-1494.
Physician's Desk Reference, 63rd Ed., 2009, 423-461, 2192-2194, 2639-2242, 3019-3022.
Pohl, et al. "Effects of flunarizine on Metrazol-induced seizures in developing rats," Epilepsy Res. Sep. 1987,1(5):302-5.
Poortman-Van Der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, 68(15):1197-1204 (2007).
Porter et al., "Report of a parent survey of cannabidiol-enriched cannabis use in pediatric treatment-resistant epilepsy," Epilepsy Behav. Dec. 2013;29(3):574-7.
Potter, "Cannabis Horticulture," Chapter 4, Handbook of Cannabis, ed. Roger G. Pertwee, pp. 65-88 (2014).
Pouton, "Lipid formulations for oral administration of drugs: non-emulsifying, self-emulsifying and 'self-microemulsifying' drug delivery systems," Eur. J. Pharm Sci, 11(Supp. 2):S93-S98 (2000).
Press et al., "Parenteral reporting of response to oral cannabis extracts for treatment of refractory epilepsy," Epilepsy Behav, 45:49-52 (2015).
Pruitt et al., "Ethanol in Liquid Preparations Intended for Children," Pediatrics, 73(3):405-407 (1984).
Raab et al., "Multiple myeloma," Lancet, 374(9686):314-339 (2009).
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutieres Syndrome," Official J Eur Paediatric Neurology Society, 18:30-37 (2014).
Rauca et al., "The role of superoxide dismutase and alpha-tocopherol in the development of seizures and kindling induced by pentylenetetrazol—influence of the radical scavenger alpha-phenyl-N-tert-butyl nitrone," Brain Research, 1009(1-2):203-212 (2004).
Resstel et al. "5-HT$_{1A}$, receptors are involved in the cannabidiol-induced attenuation of behavioural and cardiovascular responses to acute restraint stress in rats," Br J Pharmacol., 156(1):181-188 (2009).
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Rubio et al., "In vivo Experimental Models of Epilepsy," Central Nervous System Agents in Medicinal Chemistry, 10:298-309 (2010).
Russo, "Taming THC: potential cannabis synergy and phytocannabinoid-termoid entourage effects," British J. of Pharm., 163:1333-1364 (2011).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
Sander, "The epidemiology of epilepsy revisited," Curr Opin Neural, 16(2):165-170 (2003).

(56) References Cited

OTHER PUBLICATIONS

Sandyk et al., "Preliminary trial of cannabidiol in Huntington's Disease," Marihuana: An International Research Report, 157-162 (1988).
Sastri et al., "Key Attributes of TKDL: Vijaya Kalpah (Apasmaranasaka)," Anandakandam 1st ed., 1952:241 (with English translation), 5 pages.
Scuderi et al., "Cannabidiol in medicine: a review of its therapeutic potential in CNS disorders," Phytother Res., 23(5):597-602 (2009).
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).
Stephenson, "In Memoriam: Professor Jean Aicardi (1926-2015)," Pediatric Neurology, 54:3-4 (2016).
Stott et al., "Cannabinoids for the pharmaceutical industry," Euphytica, 140:83-93 (2004).
Strickley, "Solubilizing Excipients in Oral and Injectable Formulations," Table VIII, Pharmaceutical Research, 21(2):201-230 (2004).
Swann et al., "The effects of seizures on the connectivity and circuitry of the developing brain," Ment Retard Dev Disabil Res Rev., 10(2):96-100 (2004).
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thomas et al., "Cannabidiol displays unexpectedly high potency as an antagonist of CB1 and CB2 receptor agonists in vitro," British J Pharmacology, 150(5):613-623 (1988).
Thumma et al., "Influence of plasticizers on the stability and release of a prpdrig of $\Delta^9$-tetrahydrocannabinol incorporated in poly (ethylene oxide) matrices," Eur J Pharmaceutics and Biopharmaceutics, 70(2):605-614 (2008).
Thurman et al., "Standards for epidemiologic studies and surveillance of epilepsy," Epilepsia, 52 (Suppl 7):2-26 (2011).
Thurston, "Avoid Charlotte's Web for Epilepsy," Jun. 26, 2014, URL <http://drthurstone.com/charlotted-web-not-safest-option-epilepsy-treatment/>, 4 pages.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia., 20:351-363 (1979).
Unimed Pharmaceuticals, Inc., "Marinol®," Jul. 2006, <https://www.accessdata.fda.gov/dmgsatfda docs/label/2006/018651s025s0261b1.pdf>, 11 pages.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Usami et al., "Synthesis and pharmacological evaluation in mice of halogenated cannabidiol derivatives," Chem Pharm Bull (Tokyo), 47(11):1641-1645 (1999).
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, 4(6):1001-1019 (2008).
Velasco et al., "Anticancer mechanisms of cannabinoids," Curr Oncol, 23(2):S23-S32 (2016).
Velisek, "Chapter 11: Models of Chemically-Induced Acute Seizures," Models of Seizures and Epilepsy, pp. 127-152 (2006).
Veliskova, "Chapter 48: Behavioral Characterization of Seizures in Rats," Models of Seizures and Epilepsy, pp. 601-611 (2006).
Vollner et al., "Haschisch XX+ [Haschisc XX+]: Cannabidivarin, a new hashish substance," Tetrahedron Letters, 10(3):145-147 (1969).
Wahle et al., "Development of Tolerance to the Anticonvulsant Effect of Valproate but not to Ethosuximide in a Rat Model of Absence Epilepsy," Eur J Pharma, 181(1-2):1-8 (1990).
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacal., 428(1):51-57 (2001).
Weston et al., "Tetrahydrocannabivarin exhibits anticonvulsant effects in a piriform cortical brain slice model of epileptiform activity," Proceedings of the British Pharm Society, Dec. 2006, retrieved on Mar. 1, 2017, URL <http://www.pA2online.org/abstrat/abstract.jsp?abid=28533>, 1 page, Abstract only.
Wikipedia.org [online], "Cannabinoid," Wikipedia, Apr. 2003, retrieved on Mar. 1, 2017, URL <https://en.wikipedia.org/wiki/Cannabinoid>, 15 pages.
Wingerchuk, "Cannabis for medical purposes: cultivating science, weeding out the fiction," Lancet, 364:315-316 (2004).
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Mnemotechny Chasopis, 6(50):21-29 (2005) (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Zhao et al., "Chapter 27: Repetitive Seizures in the Immature Brain," Models of Seizures and E[epilepsy, 341-350 (2006).
Zhornitsky & Potvin, "Cannabidiol in Humans—The Quest for Therapeutic Targets," Pharmaceuticals, 5:529-552 (2012).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).

* cited by examiner

Graph depicting the area under the curve (AUC) for the 7-COOH CBD metabolite from the bioavailability study
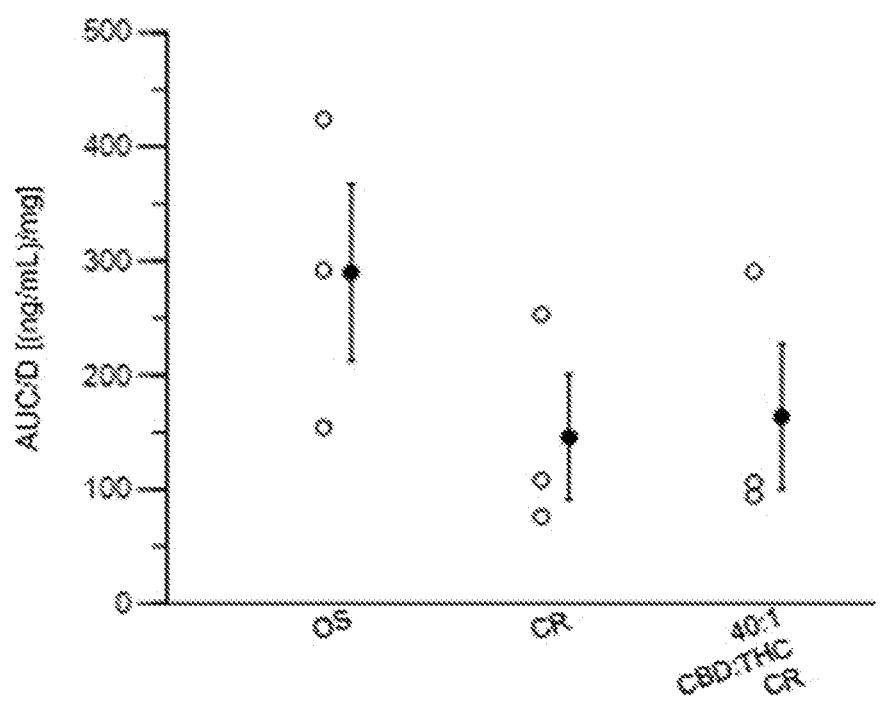

PH DEPENDENT RELEASE COATED MICROPARTICLE CANNABINOID FORMULATIONS

BACKGROUND TO THE INVENTION

Cannabinoids are lipophilic substances that are known to be poorly soluble in water (less than 1 μg/mL), and consequently have low bioavailability. In contrast, and by way of example, cannabidiol (CBD) is soluble in ethanol at 36 mg/mL and the polar solvent dimethyl sulfoxide (DMSO) at 60 mg/mL.

The contemporary use of cannabinoids in medicine has necessitated finding more effective ways of delivering these poorly soluble compounds. In addition to poor aqueous solubility cannabinoids are also known to have limited bioavailability and poor stability in formulations.

If cannabinoids are required to be provided at relatively high doses (in daily amounts of up to 2000 mg) and/or in challenging patient groups, e.g. young children, and/or for particular indications this can create further challenges.

Due to the lack of solubility, available cannabinoid formulations utilize alcohol and/or oil based excipients. The presence of alcohol in formulations is problematic, because cannabinoids (e.g., cannabidiol) are currently prescribed for rare forms of epilepsy in children. Current recommendations suggest that children should not have a blood alcohol concentration (BAC) which exceeds 0.25 g/L following a dose of an alcohol-containing medication. Furthermore, the use of oil in formulations causes gastrointestinal side effects such as diarrhoea which can be so severe it may cause the patient to discontinue use of the medication.

Clearly there is a need to have oral formulations (as opposed to injectables which are not designed for, nor indeed suitable for, oral delivery) which are more bioavailable, and which can deliver sufficient amounts of cannabinoids (greater than 0.5%, more preferably still at least 1% by wt) in a patient friendly formulation.

In addition to the problems with the use of ethanol, or an oil-based excipient, in cannabinoid containing oral formulations, the strong bitter taste of cannabinoids provides a further problem which needs to be overcome when producing an oral cannabinoid formulation. Children prefer sweet, flavoured products, such as syrups, to mask the taste of bitter drugs. However, sweeteners are generally polar, and therefore are not soluble in the oil required to solubilize the cannabinoid. High amounts of ethanol are required to solubilize the sweetener and formulate a homogenous composition.

As mentioned above, for paediatric products aimed at younger children, it is desirable to have low or no ethanol formulations.

Cannabinoids are also known to metabolise quickly, particularly when delivered as an oral solution. For example, the cannabinoid cannabidiol (CBD) quickly degrades in the body to 7-hydroxy cannabidiol (7-OH CBD) which then subsequently degrades to 7-carboxy cannabidiol (7-COOH CBD). In the treatment of epilepsy, it is known that the 7-OH metabolite is active but the 7-COOH metabolite (which is the final metabolite) is inactive, and as such the rapid degradation from CBD to 7-COOH CBD is unwanted and requires more active to be provided to successfully treat a patient.

Consequently, slowing down the metabolism of the cannabinoid would enable a medicament that produces better bioavailability and would allow for lower doses of medicine to be provided.

Specifically, drug delivery to the colon or intestines is desirable.

The approaches for colon specific drug delivery are to utilize excipients that interact with one or more aspects of the gastrointestinal system. In addition, the formulation must be able to resist digestion within the stomach.

An object of the present invention was to develop alternative cannabinoid containing formulations which were gastric resistant and able to deliver cannabinoids to the enteric or colonic areas. Such formulations must provide good bioavailability and stability of the cannabinoid active in order to be viable for drug development.

BRIEF SUMMARY OF THE DISCLOSURE

Described herein are microparticulates comprising cannabinoids. In embodiments, the microparticulates include a component which enables targeted delivery to the colon or intestines and avoid digestion (or degradation) in the stomach.

In one embodiment the invention provides a formulation in the form of a suspension comprising microparticulates which comprise the active agent of a cannabinoid in addition to excipients which enable targeted delivery to the colon or intestines and avoid digestion in the stomach.

In a further embodiment the invention provides a formulation which comprises a granulate. The granulate comprises the cannabinoid microparticulate but may be used to produce alternative dosage forms such as tablets, disintegrating tablets, filled capsules and sprinkles.

In accordance with a first aspect of the present invention there is provided a microparticulate cannabinoid containing formulation comprising one or more cannabinoids and a pH dependent release polymer (also referred to herein as a "enteric polymer").

The one or more cannabinoids may be selected from the group consisting of: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA).

The one or more cannabinoids may be a pure, isolated or synthetic cannabinoid. Alternatively, the one or more cannabinoids may be present as a botanical drug substance.

In a further aspect of the invention the one or more cannabinoids are present as a mixture of a purified, isolated or synthetic cannabinoid and a botanical drug substance.

In embodiments, the pH dependent release polymer is selected from the group consisting of: a copolymer of methacrylic acid and methacrylate, a copolymer of methacrylic acid and methyl methacrylate (Eudragit), a copolymer of methacrylic acid and ethylacrylate, hydroxypropyl methyl cellulose acetate succinate (HPMCAS), hydroxypropyl methyl cellulose phthalate (HPMCP), polyvinyl acetate phthalate (PVAP), a copolymer of methyl vinyl ether and maleic anhydride, cellulose acetate phthalate (CAP), cellulose acetate butyrate (CAB), cellulose acetate trimellitate (CAT), cellulose acetate succinate (CAS), ethyl cellulose, methyl cellulose, shellac, gellan gum, zein, alginic acid and waxes.

In embodiments, the pH dependent release polymer is HPMCAS or Eudragit.

In embodiments, the pH dependent release polymer is taken from the group consisting of: HPMCAS-L; HPMCAS-M; HPMCAS-H; Eudragit S100; Eudragit L100.

In embodiments, the microparticulate cannabinoid containing formulation further comprises one or more wetting agents.

In embodiments, the one or more wetting agents is taken from the group consisting of: poloxamers; poloxamer 188; and sodium carbonate.

In embodiments, the formulation further comprises one or more suspending agents.

In embodiments, one or more suspending agents are taken from the group consisting of: polysorbate 20; glycerol; and xanthan gum.

In embodiments, the formulation further comprises one or more pH buffers.

In embodiments, the one or more pH buffers are taken from the group consisting of: citric acid; sodium phosphate dibasic; sodium hydroxide; and phosphate buffered saline.

In embodiments, the formulation further comprises one or more preservatives.

In embodiments, the one or more preservatives are taken from the group consisting of: potassium sorbate; and sodium benzoate.

In embodiments, the formulation further comprises one or more antioxidants.

In embodiments, the one or more antioxidants are taken from the group consisting of: butylated hydroxyltoluene; butylated hydroxylanisole; alpha-tocopherol (Vitamin E); ascorbyl palmitate; ascorbic acid; sodium ascorbate; ethylenediamino tetraacetic acid; cysteine hydrochloride; citric acid; sodium citrate; sodium bisulfate; sodium metabisulfite; lecithin; propyl gallate; sodium sulfate; monothioglycerol and mixtures thereof.

In embodiments, the formulation further comprises one or more solvents.

In embodiments, the one or more solvents is taken from the group consisting of: water; ethanol and acetone.

In embodiments, the one or more cannabinoids are present in an amount of from about 10 to 50 wt %, based on the pharmaceutical formulation, preferably from about 10 to 30 wt %, more preferably from about 20 to 30 wt %.

In embodiments, a plurality of microparticulates are formulated as an oral dosage form. In embodiments, formulation is an oral dosage form selected from the group consisting of a mucoadhesive gel; a tablet; a powder; a liquid gel capsule; a solid capsule; an oral solution; an oral suspension; a granulate; and an extrudate.

In a further aspect of the present invention the microparticulate cannabinoid containing formulation is for use in the treatment of conditions requiring the administration of a neuroprotectant or anti-convulsive medication.

In embodiments, the formulation is for use in the treatment of seizures.

In embodiments, the formulation is for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, cannabis use disorder, post-traumatic stress disorder, anxiety, early psychosis, Alzheimer's disease, and autism.

In a second aspect of the present invention there is provided a method of preparing a microparticulate cannabinoid containing formulation according to any of the preceding claims, comprising spray drying the formulation.

In a third aspect of the present invention there is provided a method of preparing a microparticulate cannabinoid containing formulation according to any of the preceding claims, comprising: Preparing a mixture of the cannabinoid and pH dependent release polymer; Producing an intermediate powder blend; Processing the intermediate powder blend through a hot melt extruder; Pelleting the extrudates; and Milling the pellets to 250-500 μm.

In embodiments, an antioxidant and/or a disintegrant is added after preparing the mixture of the cannabinoid and pH dependent release polymer.

In a fourth aspect of the present invention there is provided method of treating a subject comprising administering a microparticulate cannabinoid containing formulation to the subject.

In embodiments, the subject is a human.

BRIEF DESCRIPTION OF THE DRAWINGS

FIG. 1 is a graph depicting the area under the curve (AUC) for the 7-COOH CBD metabolite from the bioavailability study.

DEFINITIONS

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis. This term includes modifying an isolated phytocannabinoid, by, for example, forming a pharmaceutically acceptable salt thereof or by the process of producing a pro-drug of a cannabinoid by the addition of one or more groups to the cannabinoid molecule to render the molecule inactive until it is metabolised within the body.

A "substantially pure" cannabinoid is defined as a cannabinoid which is present at greater than 95% (w/w) pure, e.g., greater than 96% (w/w) through 97% (w/w) thorough 98% (w/w) to 99% % (w/w) and greater. In this situation, w/w refers to the weight of the cannabinoid relative to the total weight of the cannabinoids, e.g., in the extract.

A "highly purified" cannabinoid is defined as a cannabinoid that has been extracted from the cannabis plant and purified to the extent that other cannabinoids and non-cannabinoid components that are co-extracted with the cannabinoids have been substantially removed, such that the highly purified cannabinoid is greater than or equal to 95% (w/w) pure.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes."

A botanical drug substance does not include a highly purified or chemically modified substance derived from natural sources. Thus, in the case of cannabis, BDS derived from cannabis plants do not include highly purified cannabinoids.

All weight percentages (i.e., "% by weight" and "wt. %" and "w/w") referenced herein, unless otherwise indicated, are measured relative to the total weight of the formulation or microparticle, depending on the context. In some embodiments, the weight percent is calculated based on the weight gain resulting from the addition of a particular component. For example, when a cannabinoid containing particle is coated with a pH dependent release polymer at 70% w/w, the pH dependent polymer adds 70% weight to the cannabinoid containing particle.

The term "microparticle" or "microparticulate" refers to particle ranging from about 1 μm and about 1000 μm in size (e.g., diameter), for example, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm, about 40 μm, about 41 μm, about 42 μm, about 43 μm, about 44 μm, about 45 μm, about 46 μm, about 47 μm, about 48 μm, about 49 μm, about 50 μm, about 51 μm, about 52 μm, about 53 μm, about 54 μm, about 55 μm, about 56 μm, about 57 μm, about 58 μm, about 59 μm, about 60 μm, about 61 μm, about 62 μm, about 63 μm, about 64 μm, about 65 μm, about 66 μm, about 67 μm, about 68 μm, about 69 μm, about 70 μm, about 71 μm, about 72 μm, about 73 μm, about 74 μm, about 75 μm, about 76 μm, about 77 μm, about 78 μm, about 79 μm, about 80 μm, about 81 μm, about 82 μm, about 83 μm, about 84 μm, about 85 μm, about 86 μm, about 87 μm, about 88 μm, about 89 μm, about 90 μm, about 91 μm, about 92 μm, about 93 μm, about 94 μm, about 95 μm, about 96 μm, about 97 μm, about 98 μm, about 99 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, about 505 μm, about 510 μm, about 515 μm, about 520 μm, about 525 μm, about 530 μm, about 535 μm, about 540 μm, about 545 μm, about 550 μm, about 555 μm, about 560 μm, about 565 μm, about 570 μm, about 575 μm, about 580 μm, about 585 μm, about 590 μm, about 595 μm, about 600 μm, about 605 μm, about 610 μm, about 615 μm, about 620 μm, about 625 μm, about 630 μm, about 635 μm, about 640 μm, about 645 μm, about 650 μm, about 655 μm, about 660 μm, about 665 μm, about 670 μm, about 675 μm, about 680 μm, about 685 μm, about 690 μm, about 695 μm, about 700 μm, about 705 μm, about 710 μm, about 715 μm, about 720 μm, about 725 μm, about 730 μm, about 735 μm, about 740 μm, about 745 μm, about 750 μm, about 755 μm, about 760 μm, about 765 μm, about 770 μm, about 775 μm, about 780 μm, about 785 μm, about 790 μm, about 795 μm, about 800 μm, about 805 μm, about 810 μm, about 815 μm, about 820 μm, about 825 μm, about 830 μm, about 835 μm, about 840 μm, about 845 μm, about 850 μm, about 855 μm, about 860 μm, about 865 μm, about 870 μm, about 875 μm, about 880 μm, about 885 μm, about 890 μm, about 895 μm, about 900 μm, about 905 μm, about 910 μm, about 915 μm, about 920 μm, about 925 μm, about 930 μm, about 935 μm, about 940 μm, about 945 μm, about 950 μm, about 955 μm, about 960 μm, about 965 μm, about 970 μm, about 975 μm, about 980 μm, about 985 μm, about 990 μm, about 995 μm, or about 1000 μm, including all values and ranges in between. In embodiments, the microparticle may have a diameter ranging from about 1 μm and about 500 μm in size, ranging from about 5 μm and about 400 μm in size, ranging from about 5 μm and about 300 μm in size, ranging from about 5 μm and about 200 μm in size, or ranging from about 5 μm and about 100 μm in size, ranging from about 5 μm and about 50 μm in size, including all values and ranges between these values. In the terms of the present invention a microparticulate comprises an active agent such as a cannabinoid in addition to one or more pH dependent release polymers.

The term "microsphere" and "microparticulate" or "microparticle" may be used interchangeably herein to refer to a particle comprising a pH dependent release particle and cannabinoid. These terms encompass microcapsules and micromatricies. Microcapsules are particles in which an entrapped substance (e.g., cannabinoid) is substantially surrounded by distinct capsule wall. Micromatrices are particles in which entrapped substance is dispersed throughout the matrix.

"Formulation" as used herein encompasses the term "composition." Accordingly, formulation may refer to a composition containing one or more cannabinoids, such as a microparticle. Additionally or alternatively, formulation may refer to a composition containing one or more cannabinoids, such as a microparticle, together with one or more pharmaceutically acceptable excipients.

A "unit dose" of refers to an amount of a formulation which is administered to a patient in a single dose and which contains a therapeutically effective amount of the one or more cannabinoids. For example, a unit dose may be one tablet or one capsule containing a formulation disclosed herein. In this example, the unit dose and formulation may be used interchangeably. A unit dose may also refer to an aliquot of a liquid composition or a plurality of sprinkles that are mixed with food. In embodiments in which the oral formulation contains sprinkles which are administered with food, the unit dose refers to the total amount of sprinkles.

The term "therapeutically effective" refers to a dosage sufficient to treat a disease or condition for which a drug is prescribed. As used herein, the terms "treating," "treatment" and "treat" include (i) preventing a particular disease or disorder from occurring in a subject who may be predisposed to the disease or disorder but has not yet been diagnosed as having it; (ii) curing, treating, or inhibiting the disease, i.e., arresting its development; or (iii) ameliorating the disease by reducing or eliminating symptoms, conditions, and/or by causing regression of the disease. In some embodiments, "treating," "treatment" and "treat" may include administering a therapeutically effective regimen as defined herein. For example, therapeutically effective doses of CBD to treating seizures in Lennox Gastaut Syndrome, Dravet Syndrome, or Tuberous Sclerosis Complex range from 5-25 mg/kg/day

DETAILED DESCRIPTION OF THE INVENTION

Active Pharmaceutical Ingredients

In embodiments, the disclosure provides improved cannabinoid containing formulations. As discussed herein, the formulation comprises a microparticulate comprising one or more cannabinoids, and one or more pharmaceutically acceptable excipients.

In embodiments, the cannabinoid is selected from the group consisting of: cannabichromene (CBC), cannabichromenic acid (CBCV), cannabidiol (CBD), cannabidiolic acid (CBDA), cannabidivarin (CBDV), Cannabidiol-C1 (CBD-C1) also known as cannabidiorcol, Cannabidiol-C4 (CBD-C4) also known as nor-cannabidiol, cannabidiol-C6 (CBD-C6), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). This list is not exhaustive and merely details the cannabinoids which are identified in the present application for reference. So far, over 100 different cannabinoids have been identified and these cannabinoids can be split into different groups as follows: Phytocannabinoids; Endocannabinoids; and Synthetic cannabinoids.

In embodiments, the formulation according to the present invention may also comprise at least one cannabinoid selected from those disclosed in Handbook of Cannabis, Roger Pertwee, Chapter 1, pages 3 to 15.

In embodiments, the formulation comprises one or more cannabinoids, which are preferably selected from the group consisting of, cannabidiol (CBD) or cannabidivarin (CBDV), tetrahydrocannabinol (THC), tetrahydrocannabivarin (THCV), cannabigerol (CBG) and cannabidiolic acid (CBDA) or a combination thereof. In embodiments, the formulation comprises cannabidiol (CBD) and/or cannabidivarin (CBDV).

In a further embodiment, the formulation comprises at least two cannabinoids. In embodiments, the at least two cannabinoids are selected from the group consisting of, cannabidiol (CBD), tetrahydrocannabinol (THC), tetrahydrocannabivarin (THCV), cannabigerol (CBG) and cannabidiolic acid (CBDA).

In embodiments, the one or more cannabinoids are present in a microparticle in an amount of from about 0.1 (% w/w) to about 50 (% w/w), based on total weight of the microparticle, e.g., about 0.1 (% w/w), about 0.2 (% w/w), about 0.3 (% w/w), about 0.4 (% w/w), about 0.5 (% w/w), about 0.6 (% w/w), about 0.7 (% w/w), about 0.8 (% w/w), about 0.9 (% w/w), about 1 (% w/w), about 2 (% w/w), about 3 (% w/w), about 4 (% w/w), about 5 (% w/w), about 6 (% w/w), about 7 (% w/w), about 8 (% w/w), about 9 (% w/w), about 10 (% w/w), about 11 (% w/w), about 12 (% w/w), about 13 (% w/w), about 14 (% w/w), about 15 (% w/w), about 16 (% w/w), about 17 (% w/w), about 18 (% w/w), about 19 (% w/w), about 20 (% w/w), about 21 (% w/w), about 22 (% w/w), about 23 (% w/w), about 24 (% w/w), about 25 (% w/w), about 26 (% w/w), about 27 (% w/w), about 28 (% w/w), about 29 (% w/w), about 30 (% w/w), about 31 (% w/w), about 32 (% w/w), about 33 (% w/w), about 34 (% w/w), about 35 (% w/w), about 36 (% w/w), about 37 (% w/w), about 38 (% w/w), about 39 (% w/w), about 40 (% w/w), about 41 (% w/w), about 42 (% w/w), about 43 (% w/w), about 44 (% w/w), about 45 (% w/w), about 46 (% w/w), about 47 (% w/w), about 48 (% w/w), about 49 (% w/w), about 50 (% w/w), inclusive of all values and range between these values. In embodiments, the one or more cannabinoids comprises about 10 to about 30 (% w/v) of the microparticle. In embodiments, the one or more cannabinoids comprises about 15 (% w/w) of the microparticle. In embodiments, the one or more cannabinoids comprises about 20 (% w/w) of the microparticle.

Microparticles comprising the cannabinoid may be prepared in any of the formulations described herein (e.g., a liquid composition such as a suspension, or a solid composition such as a tablet or sprinkles). In embodiments, the one or more cannabinoids are present in an amount of from about 0.1 (% w/v) to about 30 (% w/v), based on the total formulation, about 0.1 (% w/v), about 0.2 (% w/v), about 0.3 (% w/v), about 0.4 (% w/v), about 0.5 (% w/v), about 0.6 (% w/v), about 0.7 (% w/v), about 0.8 (% w/v), about 0.9 (% w/v), about 1 (% w/v), about 2 (% w/v), about 2.5 (% w/v), about 3 (% w/v), about 4 (% w/v), about 5 (% w/v), about 6 (% w/v), about 7 (% w/v), about 8 (% w/v), about 9 (% w/v), about 10 (% w/v), about 11 (% w/v), about 12 (% w/v), about 13 (% w/v), about 14 (% w/v), about 15 (% w/v), about 16 (% w/v), about 17 (% w/v), about 18 (% w/v), about 19 (% w/v), about 20 (% w/v), about 21 (% w/v), about 22 (% w/v), about 23 (% w/v), about 24 (% w/v), about 25 (% w/v), about 26 (% w/v), about 27 (% w/v), about 28 (% w/v), about 29 (% w/v), about 30 (% w/v) of the formulation. In embodiments, the one or more cannabinoids comprises about 1 to about 5 (% w/v) of the total formulation, or about 2-5 (% w/v) of the total formulation. In embodiments, the one or more cannabinoids comprises about 3 (% w/v) of the total formulation. In embodiments, the one or more cannabinoids comprises about 2.5 (% w/v) of the total formulation.

In embodiments, the one or more cannabinoids are present in an amount of from about 0.1 (% w/w) to about 30 (% w/w), based on the total formulation, about 0.1 (% w/w), about 0.2 (% w/w), about 0.3 (% w/w), about 0.4 (% w/w), about 0.5 (% w/w), about 0.6 (% w/w), about 0.7 (% w/w), about 0.8 (% w/w), about 0.9 (% w/w), about 1 (% w/w), about 2 (% w/w), about 2.5 (% w/w), about 3 (% w/w), about 4 (% w/w), about 5 (% w/w), about 6 (% w/w), about 7 (% w/w), about 8 (% w/w), about 9 (% w/w), about 10 (% w/w), about 11 (% w/w), about 12 (% w/w), about 13 (% w/w), about 14 (% w/w), about 15 (% w/w), about 16 (% w/w), about 17 (% w/w), about 18 (% w/w), about 19 (% w/w), about 20 (% w/w), about 21 (% w/w), about 22 (% w/w), about 23 (% w/w), about 24 (% w/w), about 25 (% w/w), about 26 (% w/w), about 27 (% w/w), about 28 (% w/w), about 29 (% w/w), about 30 (% w/w), of the formulation. In embodiments, the one or more cannabinoids comprises about 3 (% w/w) of the total formulation. In embodiments, the one or more cannabinoids comprises about 2.5 (% w/w) of the total formulation.

In embodiments, the one or more cannabinoid is synthetic or highly purified from its natural source (for example, plant derived recrystallized form). When a highly purified source is used, it is purified such that the one or more cannabinoid is present at greater than 95%, more preferably 98% of the total extract (w/w). In embodiments, the CBD has a purity of greater than 95% (w/w) CBD. In embodiments, the CBD has a purity of greater than 98% (w/w) CBD. In embodiments, the THCV has a purity of greater than 95% (w/w) THCV. In embodiments, the THCV has a purity of greater than 98% (w/w) THCV.

In some embodiments, the compositions of the disclosure comprise CBD, at purity of at least 95% w/w (e.g., 98% w/w, or 99% w/w), and one or more of CBDA, CBDV, THC and CBD-C4. In some embodiments, the CBDA is present in an amount of about 0.15% w/w or less, e.g., about 0.15% w/w, about 0.1% w/w, about 0.05% w/w, or about 0.01% w/w, inclusive of all values and ranges between these values. In some embodiments, CBDV is present in an amount of about 1.0% w/w or less, e.g., about 1.0% w/w or less, about 0.9% w/w, about 0.8% w/w, about 0.7% w/w, about 0.6% w/w, about 0.5% w/w, about 0.4% w/w, about 0.3% w/w, about 0.2% w/w, about 0.1% w/w, about 0.09% w/w, about 0.08% w/w, about 0.07% w/w, about 0.06% w/w, about 0.05% w/w, about 0.04% w/w, about 0.03% w/w, about 0.02% w/w, about 0.01% w/w, inclusive of all values and ranges between these values. In some embodiments, THC is present in an amount of about 0.15% w/w or less, e.g., about 0.15% w/w, about 0.1% w/w, about 0.05% w/w, or about 0.01% w/w, inclusive of all values and ranges between these values. In some embodiments, CBD-C4 is present in an amount of about 0.5% w/w or less, e.g., about 0.5% w/w, about 0.4% w/w, about 0.3% w/w, about 0.2% w/w, about 0.1% w/w, about 0.09% w/w, about 0.08% w/w, about 0.07% w/w, about 0.06% w/w, about 0.05% w/w, about 0.04% w/w, about 0.03% w/w, about 0.02% w/w, about 0.01% w/w, inclusive of all values and ranges between these values. Other cannabinoids may also be present.

In a further embodiment, the one or more cannabinoids are present as a complex mixture or as a botanical drug substance (BDS). When present as such as mixture the major cannabinoid is present in addition to all the other cannabinoid and non-cannabinoid components that are co-extracted with the major cannabinoid. THC BDS and CBD BDS have been characterized in the patent application WO 2007/083098 which is incorporated by reference herein in its entirety.

In a further embodiment the formulation comprises a mixture of a cannabinoid which is present as a highly purified (>96%, or >98%) or synthetic form, in combination with a cannabinoid which is present as a complex mixture or a BDS.

In embodiments, the oral formulation (e.g., liquid composition such as a slurry or suspension) comprises from about 0.001 to about 350 mg/mL of cannabinoid, for example, about 0.001 mg/mL, about 0.005 mg/mL, about 0.01 mg/mL, about 0.015 mg/mL, about 0.02 mg/mL, about 0.025 mg/mL, about 0.03 mg/mL, about 0.035 mg/mL, about 0.04 mg/mL, about 0.045 mg/mL, about 0.05 mg/mL, about 0.055 mg/mL, about 0.06 mg/mL, about 0.065 mg/mL, about 0.07 mg/mL, about 0.075 mg/mL, about 0.08 mg/mL, about 0.085 mg/mL, about 0.09 mg/mL, about 0.095 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL, about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL, about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL, about 92 mg/mL, about 93 mg/mL, about 94 mg/mL, about 95 mg/mL, about 96 mg/mL, about 97 mg/mL, about 98 mg/mL, about 99 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, about 280 mg/mL, about 285 mg/mL, about 290 mg/mL, about 295 mg/mL, about 300 mg/mL, about 305 mg/mL, about 310 mg/mL, about 315 mg/mL, about 320 mg/mL, about 325 mg/mL, about 330 mg/mL, about 335 mg/mL, about 340 mg/mL, about 345 mg/mL, or about 350 mg/mL. In embodiments, the oral pharmaceutical formulation comprises about 1 mg/mL to about 350 mg/mL of cannabinoids. In embodiments, the oral pharmaceutical formulation comprises between about 25 mg/mL and about 100 mg/mL of cannabinoids.

In embodiments, the unit dose comprises ranging from about 5 mg and about 5000 mg of cannabinoid, for example, about 5 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg, about 1510 mg, about 1520 mg, about 1530 mg, about 1540 mg, about 1550 mg, about 1560 mg, about 1570 mg, about 1580 mg, about 1590 mg, about 1600 mg, about 1610 mg, about 1620 mg, about 1630 mg, about 1640 mg, about 1650 mg, about 1660 mg, about 1670 mg, about 1680 mg, about 1690 mg, about 1700 mg, about 1710 mg, about 1720 mg, about 1730 mg, about 1740 mg, about 1750 mg, about 1760 mg, about 1770 mg, about 1780 mg, about 1790 mg, about 1800 mg, about 1810 mg, about 1820 mg, about 1830 mg, about 1840 mg, about 1850 mg, about 1860 mg, about 1870 mg, about 1880 mg, about 1890 mg, about 1900 mg, about 1910 mg, about 1920 mg, about 1930 mg, about 1940 mg, about 1950 mg, about 1960 mg, about 1970 mg, about 1980 mg, about 1990 mg, about 2000 mg, 201 about 2110 mg, about 2120 mg, about 2130 mg, about 2140 mg, about 2150 mg, about 2160 mg, about 2170 mg, about 2180 mg, about 2190 mg, about 2200 mg, about 2210 mg, about 2220 mg, about 2230 mg, about 2240 mg, about 2250 mg, about 2260 mg, about 2270 mg, about 2280 mg, about 2290 mg, about 2300 mg, about 2310 mg, about 2320 mg, about 2330 mg, about 2340 mg, about 2350 mg, about 2360 mg, about 2370 mg, about 2380 mg, about 2390 mg, about 2400 mg, about 2410 mg, about 2420 mg, about 2430 mg, about 2440 mg, about 2450 mg, about 2460 mg, about 2470 mg, about 2480 mg, about 2490 mg, about 2500 mg, about 2510 mg, about 2520 mg, about 2530 mg, about 2540 mg, about 2550 mg, about 2560 mg, about 2570 mg, about 2580 mg, about 2590 mg, about 2600 mg, about 2610 mg, about 2620 mg, about 2630 mg, about 2640 mg, about 2650 mg, about 2660 mg, about 2670 mg, about 2680 mg, about 2690 mg, about 2700 mg, about 2710 mg, about 2720 mg, about 2730 mg, about 2740 mg, about 2750 mg, about 2760 mg, about 2770 mg, about 2780 mg, about 2790 mg, about 2800 mg, about 2810 mg, about 2820 mg, about 2830 mg, about 2840 mg, about 2850 mg, about 2860 mg, about 2870 mg, about 2880 mg, about 2890 mg, about 2900 mg, about 2910 mg, about 2920 mg, about 2930 mg, about 2940 mg, about 2950 mg, about 2960 mg, about 2970 mg, about 2980 mg, about 2990 mg, about 3000 mg, about 3100 mg, about 3200 mg, about 3300 mg, about 3400 mg, about 3500 mg, about 3600 mg, about 3700 mg, about 3800 mg, about 3900 mg, about 4000 mg, about 4100 mg, about 4200 mg, about 4300 mg, about 4400 mg, about 4500 mg, about 4600 mg, about 4700 mg, about 4800 mg, about 4900 mg, or about 5000 mg cannabinoid, including all values and ranges in between. In embodiments, a unit of the oral cannabinoid formulation comprises about 10 mg to about 1000 mg of cannabinoid. In embodiments, a unit of the oral cannabinoid formulation comprises from about 50 mg to about 500 mg of cannabinoid.

In embodiments, after administering between about 1 mg/kg/day and about 25 mg/kg/day of a cannabinoid in a formulation of the present disclosure (e.g. about 1.0 mg/kg/day, about 2.0 mg/kg/day, about 2.5 mg/kg/day, about 3.0 mg/kg/day, about 3.5 mg/kg/day, about 4.0 mg/kg/day, about 5.0 mg/kg/day, about 6.0 mg/kg/day, about 7.5 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, or about 25 mg/kg/day), the patient has an steady state area under the concentration time curve from time zero (t1) to five hours (t2) ($AUC_{t1-t2}$) between 25 ng*hr/mL and 4000 ng*hr/mL. In some embodiments, the $AUC_{t1-t2}$ is about 25 ng*hr/mL, about 50 ng*hr/mL, about 75 ng*hr/mL, about 100 ng*hr/mL, about 125 ng*hr/mL, about 150 ng*hr/mL, about 175 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, and about 400 ng*hr/mL, about 500 ng*hr/mL, about 600 ng*hr/mL, about 700 ng*hr/mL, about 800 ng*hr/mL, about 900 ng*hr/mL, about 1000 ng*hr/mL, about 1100 ng*hr/mL, about 1200 ng*hr/mL, about 1300 ng*hr/mL, about 1400 ng*hr/mL, about 1500 ng*hr/mL, about 1600 ng*hr/mL, about 1700 ng*hr/mL, about 1800 ng*hr/mL, about 1900 ng*hr/mL, about 2000 ng*hr/mL, about 2100 ng*hr/mL, about 2200 ng*hr/mL, about 2300 ng*hr/mL, about 2400 ng*hr/mL, about 2500 ng*hr/mL, about 2600 ng*hr/mL, about 2700 ng*hr/mL, about 2800 ng*hr/mL, about 2900 ng*hr/mL, about 3000 ng*hr/mL, about 3100 ng*hr/mL, about 3200 ng*hr/mL, about 3300 ng*hr/mL, about 3400 ng*hr/mL, about 3500 ng*hr/mL, about 3600 ng*hr/mL, about 3700 ng*hr/mL, about 3800 ng*hr/mL, about or about 3900 ng*hr/mL, about or about 4000 ng*hr/mL, including all ranges and values in between. In some embodiments, the $AUC_{t1-t2}$ is ranges from about 80% to about 125% of the aforementioned values.

In some embodiments, the unit dose of the present disclosure comprises a dose of CBD that is equivalent to 25 mg/kg. In such embodiments, after administration of a dose equivalent to 25 mg/kg, the $AUC_{t1-t2}$ ranges from about 80% to about 125% of about 2520 (52.4%) ng*hr/mL (reported as a geometric mean (% coefficient of variation)). In some embodiments, the patient has an $AUC_{t1-t2}$ ranges from about 2000 ng*hr/mL to about 3500 ng*hr/mL, for example, about 2000 ng*hr/mL, about 2100 ng*hr/mL, about 2200 ng*hr/mL, about 2300 ng*hr/mL, about 2400 ng*hr/mL, about 2500 ng*hr/mL, about 2600 ng*hr/mL, about 2700 ng*hr/mL, about 2800 ng*hr/mL, about 2900 ng*hr/mL, about 3000 ng*hr/mL, about 3100 ng*hr/mL, about 3200 ng*hr/mL, about 3300 ng*hr/mL, about 3400 ng*hr/mL, or about 3500 ng*hr/mL, including all values and ranges in between. In some embodiments, after administration of CBD, the $AUC_{t1-t2}$ is less than or equal to $AUC_{t1-t2}$ of 50 mg/kg of CBD—i.e., less than or equal to 2730 (87.2%) ng*hr/mL (e.g., less than 2700 ng*hr/mL, 2600 ng*hr/mL, 2500 ng*hr/mL, 2400 ng*hr/mL, 2300 ng*hr/mL, 2200 ng*hr/mL, 2100 ng*hr/mL, 2000 ng*hr/mL, 1900 ng*hr/mL, 1800 ng*hr/mL, 1700 ng*hr/mL, 1600 ng*hr/mL, 1500 ng*hr/mL, 1400 ng*hr/mL, 1300 ng*hr/mL, 1200 ng*hr/mL, 1100 ng*hr/mL, or 1000 ng*hr/mL, etc).

In some embodiments, the unit dose of the present disclosure comprises a dose of CBD that is equivalent to 5 mg/kg. In such embodiments, after administration of a dose equivalent to 5 mg/kg, the steady state AUC from time zero to the last detectable dose (t) ($AUC_{0-t}$) ranges from about 80% to about 125% of about 241 (101) ng*hr/mL. In some embodiments, the $AUC_{0-t}$ is ranges from about 170 ng*hr/mL to about 350 ng*hr/mL, for example, about 170 ng*hr/mL, about 180 ng*hr/mL, about 190 ng*hr/mL, about 200 ng*hr/mL, about 210 ng*hr/mL, about 220 ng*hr/mL, about 230 ng*hr/mL, about 240 ng*hr/mL, about 250 ng*hr/mL, about 260 ng*hr/mL, about 270 ng*hr/mL, about 280 ng*hr/mL, about 290 ng*hr/mL, about 300 ng*hr/mL, about 310 ng*hr/mL, about 320 ng*hr/mL, about 330 ng*hr/mL, about 340 ng*hr/mL, and about 350 ng*hr/mL, including all values and ranges in between.

In some embodiments, the unit dose of the present disclosure comprises a dose of CBD that is equivalent to 10 mg/kg. In such embodiments, after administration of a dose equivalent to 10 mg/kg, the patient has an $AUC_{0-t}$ ranging from about 80% to about 125% of about 722 (79.9) ng*hr/mL. In such embodiments, the patient has an $AUC_{0-t}$ ranging from about 550 ng*hr/mL to about 950 ng*hr/mL, for example, about 550 ng*hr/mL, about 570 ng*hr/mL, about 590 ng*hr/mL, about 610 ng*hr/mL, about 630 ng*hr/mL, about 650 ng*hr/mL, about 670 ng*hr/mL, about 690 ng*hr/mL, about 710 ng*hr/mL, about 730 ng*hr/mL, about 750 ng*hr/mL, about 770 ng*hr/mL, about 790 ng*hr/mL, about 810 ng*hr/mL, about 830 ng*hr/mL, about 850 ng*hr/mL, about 870 ng*hr/mL, about 890 ng*hr/mL, about 910 ng*hr/mL, about 930 ng*hr/mL, or about 950 ng*hr/mL, including all values and ranges in between.

In some embodiments, the unit dose of the present disclosure comprises a dose of CBD that is equivalent to 20 mg/kg. In such embodiments, after administration of a dose equivalent to 20 mg/kg, the patient has an $AUC_{0-t}$ that ranges from about 80% to about 125% of about 963 (93.4) ng*hr/mL. In such embodiments, the patient has an $AUC_{0-t}$ ranging from about 700 ng*hr/mL to about 1300 ng*hr/mL, for example, about 700 ng*hr/mL, about 720 ng*hr/mL, about 740 ng*hr/mL, about 760 ng*hr/mL, about 780 ng*hr/mL, about 800 ng*hr/mL, about 820 ng*hr/mL, about 840 ng*hr/mL, about 860 ng*hr/mL, about 880 ng*hr/mL, about 900 ng*hr/mL, about 920 ng*hr/mL, about 940 ng*hr/mL, about 960 ng*hr/mL, about 980 ng*hr/mL, about 1000 ng*hr/mL, about 1020 ng*hr/mL, about 1040 ng*hr/mL, about 1060 ng*hr/mL, about 1080 ng*hr/mL, about 1100 ng*hr/mL, about 1120 ng*hr/mL, about 1140 ng*hr/mL, about 1160 ng*hr/mL, about 1180 ng*hr/mL, about 1200 ng*hr/mL, about 1220 ng*hr/mL, about 1240 ng*hr/mL, about 1260 ng*hr/mL, about 1280 ng*hr/mL, or about 1300 ng*hr/mL, including all values and ranges in between.

In some embodiments, the dosage form provides a pharmacokinetic profile that is bioequivalent to Epidiolex. In some embodiments, the dosage form provides an AUC that is within about 80%-125% of the AUC of an equivalent dose of Epidiolex®. The dosage form of claim 9 or 10, comprising CBD, wherein after administration, the dosage form provides an AUC that is within about 80%-125% of the Cmax of an equivalent dose of Epidiolex®. Epidiolex® is an immediate release formulation containing CBD. Epidiolex® is currently available as an oral solution, which comprises about 100 mg/mL CBD. The formulation comprises dehydrated alcohol (e.g., ethanol), sesame oil, a flavorant (e.g., strawberry flavour), and a sweetener (e.g., sucralose). The concentration of ethanol may range from about 71.1 mg/mL to about 86.9 mg/mL; the concentration of the sweetener may range from about 0.45 mg/mL to about 0.55 mg/mL; the concentration of flavoring may range from about 0.18 mg/mL to about 0.22 mg/mL; and sesame oil is added, q.s. to about 1.0 mL.

Excipients

The compositions described herein can include one or more pharmaceutically acceptable excipients. Non-limiting examples of pharmaceutically acceptable excipients include pH dependent release polymer, extended release polymer, adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier. Pharmaceutically acceptable excipients may be described in Remington's Pharmaceutical Sciences, $18^{th}$ Edition, which is herein incorporated by reference in its entirety.

In embodiments, the microparticulate comprises one or more of the following excipients.

pH Dependent Release Polymers:

In embodiments, the cannabinoid formulations described herein comprise one or more pH dependent polymers or copolymers thereof. In embodiments, the formulations described herein comprise from about 5% w/w to about 85% w/w of a pH dependent release polymer or copolymer thereof, for example, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, or about 85% w/w, including all values and ranges there between, based on the weight of the microparticle. In embodiments, the cannabinoid formulations described herein comprise one or more pH dependent polymers or copolymers thereof. In embodiments, the formulations described herein comprise from about 10% w/w to about 80% w/w of a pH dependent release polymer or copolymer thereof, In embodiments, the formulations comprise about 75% w/w of a pH dependent release polymer. In embodiments, the formulations comprise about 78% w/w of a pH dependent release polymer. In embodiments, the formulations comprise about 80% of a pH dependent release polymer. In embodiments, the formulations comprise about 63% of a pH dependent release polymer. In embodiments, the formulations comprise about 11% of a pH dependent release polymer. In embodiments, the formulations comprise about 13% of a pH dependent release polymer.

The pH dependent release polymers of the present invention are used to enable release of the active agent at a pH of either pH 6 (intestines) or pH 7 (colon) rather than at an acidic pH (such as occurs in the stomach). pH dependent release polymers may be selected to begin releasing the cannabinoid around pH 5.5, 6.0 or 7.0.

In embodiments, the polymers are selected from polymethacrylate derivatives (such as a copolymer of methacrylic acid and methacrylate, a copolymer of methacrylic acid and methyl methacrylate or a copolymer of methacrylic acid and ethylacrylate); hypromellose derivatives (such as hydroxypropyl methyl cellulose acetate succinate (HPMCAS) and hydroxypropyl methyl cellulose phthalate (HPMCP)); polyvinylacetate derivatives (such as polyvinyl acetate phthalate (PVAP)); polyvinylether derivatives (such as a copolymer of methyl vinyl ether and maleic anhydride); cellulose derivatives (such as cellulose acetate phthalate (CAP), cellulose acetate terephthalate, cellulose acetate isophthalate, cellulose acetate butyrate (CAB), cellulose acetate trimellitate (CAT), cellulose acetate succinate (CAS), ethyl cellulose, methyl cellulose); shellac, gellan gum, zein, alginic acid, waxes and mixtures thereof.

In embodiments, the pH dependent polymer is HPMCAS. In embodiments, the pH dependent polymer is a copolymer of methacrylic acid and methyl methacrylate. In embodiments, the ratio of methacrylic acid to methyl methacrylate is ranges from about 1:10 to about 10:1, for example, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or about 10:1 by weight. The copolymer of methacrylic acid and methyl methacrylate is known under the tradename Eudragit®. Two forms of Eudragit are known: L100 and S100. The L100 is a copolymer of the two compounds in a 1:1 ratio and the S100 additionally comprises 0.3% sodium laurylsulfate. In embodiments, the formulation comprises Eudragit L100. In embodiments, the formulation comprises Eudragit S100.

Hydroxypropyl Methylcellulose Acetate Succinate (HPMCAS)

HPMCAS is a cellulose derived polymer containing acetyl and succinoyl groups. It is an enteric polymer which dissolves at a pH range of from about 5.5 to about 6.5 depending on the ratio of acetyl and succinoyl groups found within the polymer.

Three grades of HPMCAS are available; HPMCAS-L, HPMCAS-M and HPMCAS-H, these polymers dissolve at pH 5.5, 6.0 and 6.5 respectively. In embodiments, the pH dependent polymer is HPMCAS-L. In embodiments, the pH dependent polymer is HPMCAS-M. In embodiments, the pH dependent polymer is HPMCAS-H.

Eudragit L100 (Methacrylic Acid and Methyl Methacrylate Copolymer (1:1))

Eudragit L100 is a copolymer comprised of methacrylic acid and methyl methacrylate in a 1:1 ratio. The ratio of methacrylic acid to methyl methacrylate controls the pH at which the polymer dissolves. In embodiments, formulations comprising Eudragit L100 releases the cannabinoid at a pH of 6.0 and above, for example, at about pH 6, pH 6.1, pH 6.2, pH 6.3, pH 6.4, pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, or pH 8

It is most commonly dispersed in an aqueous base to be spray coated onto tablets or capsules to give them an enteric coating. In embodiments, Eudragit L100 is a solubility enhancer.

Eudragit S100 (Methacrylic Acid and Methyl Methacrylate Copolymer (1:2))

Eudragit L100 is a copolymer comprised of methacrylic acid and methyl methacrylate in a 1:2 ratio. In embodiments, formulations comprising Eudragit S100 release cannabinoid at a pH of 7.0 and above, for example, pH 7, pH 7.1, pH 7.2, pH 7.3, pH 7.4, pH 7.5, pH 7.6, pH 7.7, pH 7.8, pH 7.9, or pH 8.

It is most commonly dispersed in an aqueous base to be spray coated onto tablets or capsules to give them a colonic coating. It can also be used as a solubility enhancer for poorly water-soluble drugs when formulated into a solid dispersion along with an API.

Wetting Agent:

In embodiments, the oral formulations comprise a wetting agent. In embodiments, the wetting agent is selected from the group consisting of poloxamers (polyoxyethylene-polyoxypropylene block copolymers); polysorbate 80 (polyoxyethylene (20) sorbitan monooleate; sodium carbonate; polyethylene glycols (PEG, e.g., Mw 1500-20,000); and hydrophilic colloids such as acacia, alginates, methycellulose; alcohols; and glycerin. In some embodiments, the wetting agent is PEG with a molecular weight ranging from about 100 mg/mol to about 20,000 g/mol, for example, about 100 g/mol, about 200 g/mol, about 300 g/mol, about 400 g/mol, about 500 g/mol, about 600 g/mol, about 700 g/mol, about 800 g/mol, about 900 g/mol, about 1000 g/mol, about 1100 g/mol, about 1200 g/mol, about 1300 g/mol, about 1400 g/mol, about 1500 g/mol, about 1600 g/mol, about 1700 g/mol, about 1800 g/mol, about 1900 g/mol, about 2000 g/mol, about 2100 g/mol, about 2200 g/mol, about 2300 g/mol, about 2400 g/mol, about 2500 g/mol, about 2600 g/mol, about 2700 g/mol, about 2800 g/mol, about 2900 g/mol, about 3000 g/mol, about 3100 g/mol, about 3200 g/mol, about 3300 g/mol, about 3400 g/mol, about 3500 g/mol, about 3600 g/mol, about 3700 g/mol, about 3800 g/mol, about 3900 g/mol, about 4000 g/mol, about 4100 g/mol, about 4200 g/mol, about 4300 g/mol, about 4400 g/mol, about 4500 g/mol, about 4600 g/mol, about 4700 g/mol, about 4800 g/mol, about 4900 g/mol, about 5000 g/mol, about 5100 g/mol, about 5200 g/mol, about 5300 g/mol, about 5400 g/mol, about 5500 g/mol, about 5600 g/mol, about 5700 g/mol, about 5800 g/mol, about 5900 g/mol, about 6000 g/mol, about 6100 g/mol, about 6200 g/mol, about 6300 g/mol, about 6400 g/mol, about 6500 g/mol, about 6600 g/mol, about 6700 g/mol, about 6800 g/mol, about 6900 g/mol, about 7000 g/mol, about 7100 g/mol, about 7200 g/mol, about 7300 g/mol, about 7400 g/mol, about 7500 g/mol, about 7600 g/mol, about 7700 g/mol, about 7800 g/mol, about 7900 g/mol, about 8000 g/mol, about 8100 g/mol, about 8200 g/mol, about 8300 g/mol, about 8400 g/mol, about 8500 g/mol, about 8600 g/mol, about 8700 g/mol, about 8800 g/mol, about 8900 g/mol, about 9000 g/mol, about 9100 g/mol, about 9200 g/mol, about 9300 g/mol, about 9400 g/mol, about 9500 g/mol, about 9600 g/mol, about 9700 g/mol, about 9800 g/mol, about 9900 g/mol, about 10000 g/mol, about 10100 g/mol, about 10200 g/mol, about 10300 g/mol, about 10400 g/mol, about 10500 g/mol, about 10600 g/mol, about 10700 g/mol, about 10800 g/mol, about 10900 g/mol, about 11000 g/mol, about 11100 g/mol, about 11200 g/mol, about 11300 g/mol, about 11400 g/mol, about 11500 g/mol, about 11600 g/mol, about 11700 g/mol, about 11800 g/mol, about 11900 g/mol, about 12000 g/mol, about 12100 g/mol, about 12200 g/mol, about 12300 g/mol, about 12400 g/mol, about 12500 g/mol, about 12600 g/mol, about 12700 g/mol, about 12800 g/mol, about 12900 g/mol, about 13000 g/mol, about 13100 g/mol, about 13200 g/mol, about 13300 g/mol, about 13400 g/mol, about 13500 g/mol, about 13600 g/mol, about 13700 g/mol, about 13800 g/mol, about 13900 g/mol, about 14000 g/mol, about 14100 g/mol, about 14200 g/mol, about 14300 g/mol, about 14400 g/mol, about 14500 g/mol, about 14600 g/mol, about 14700 g/mol, about 14800 g/mol, about 14900 g/mol, about 15000 g/mol, about 15100 g/mol, about 15200 g/mol, about 15300 g/mol, about 15400 g/mol, about 15500 g/mol, about 15600 g/mol, about 15700 g/mol, about 15800 g/mol, about 15900 g/mol, about 16000 g/mol, about 16100 g/mol, about 16200 g/mol, about 16300 g/mol, about 16400 g/mol, about 16500 g/mol, about 16600 g/mol, about 16700 g/mol, about 16800 g/mol, about 16900 g/mol, about 17000 g/mol, about 17100 g/mol, about 17200 g/mol, about 17300 g/mol, about 17400 g/mol, about 17500 g/mol, about 17600 g/mol, about 17700 g/mol, about 17800 g/mol, about 17900 g/mol, about 18000 g/mol, about 18100 g/mol, about 18200 g/mol, about 18300 g/mol, about 18400 g/mol, about 18500 g/mol, about 18600 g/mol, about 18700 g/mol, about 18800 g/mol, about 18900 g/mol, about 19000 g/mol, about 19100 g/mol, about 19200 g/mol, about 19300 g/mol, about 19400 g/mol, about 19500 g/mol, about 19600 g/mol, about 19700 g/mol, about 19800 g/mol, about 19900 g/mol, or about 20000 g/mol, In embodiments, the formulations described herein comprise from about 0.1% w/w to about 30% w/w of a wetting agent, for example, about 0.1% w/w, about 0.2% w/w, about 0.3% w/w, about 0.4% w/w, about 0.5 w/w, about 0.6% w/w, about 0.7% w/w, about 0.8% w/w, about 0.9% w/w, about 1 w/w, about 1.5 w/w, about 2% w/w, about 2.5% w/w, about 3% w/w, about 3.5 w/w, about 4% w/w, about 4.5 w/w, about 5 w/w, about 5.5% w/w, about 6% w/w, about 6.5% w/w, about 7% w/w, about 8% w/w, about 8.5 w/w, about 9% w/w, about 9.5 w/w, about 10% w/w about 11 w/w, about 12% w/w, about 13% w/w, about 14% w/w, about 15 w/w, about 16% w/w, about 17% w/w, about 18% w/w, about 19% w/w, about 20% w/w, about 21% w/w, about 22% w/w, about 23% w/w, about 24% w/w, about 25 w/w, about 26% w/w, about 27% w/w, about 28% w/w, about 29% w/w, or about 30% w/w of a wetting agent. In embodiments, the formulations comprise about 5% w/w of a wetting agent. In embodiments, the formulations comprise about 20% w/w of a wetting agent. In embodiments, the formulations comprise about 0.75 w/w of a wetting agent.

Poloxamer 188

In embodiments, the wetting agent is a nonionic triblock copolymers composed of a central hydrophobic chain of polyoxypropylene (poly(propylene oxide)) flanked by two hydrophilic chains of polyoxyethylene (poly(ethylene oxide)). These block copolymers may be referred as poloxamers. In some embodiments, the poloxamer is poloxamer 188.

Poloxamer 188 is a nonionic linear copolymer having an average molecular weight of 8400 Daltons. Poloxamer 188 is an amphiphilic co-polymer that has multifunctionality. In embodiments, poloxamer 188 in the formulations described herein serves as a solubilizer, emulsifier, or as a wetting agent. Poloxamer 188 has an HLB value of 29 meaning it is highly hydrophilic.

Suspending Agents:

In embodiments, the formulations described herein comprise one or more suspending agents. In embodiments, the formulations described herein include anionic, cationic, and nonionic polymers. Non-limiting examples of such polymers include but are not limited to vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageen, pectin, agar, quince seed (*Cyclonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, long chain amine oxides, ethylene glycol esters of fatty acids, vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageen, pectin, agar, quince seed (*Cyclonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, and polyethyleneimine, N,N-dihydrocarbyl amido benzoic acid, PS20, glycerol, and xanthan gum.

In embodiments, the formulations described herein comprise from about 0.1% w/w to about 50% w/w of a suspending agent, for example, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, or about 50% w/w of a suspending agent. In embodiments, the formulations comprise about 0.2% w/w suspending agent. In embodiments, the formulations comprise about 20% w/w suspending agent.

Polysorbate 20 (Tween 20)

In embodiments, formulations comprise Tween 20. In embodiments, Tween 20 serves as an emulsifier, wetting, agent, solubilizer, or suspending agent. Tween 20 is a nonionic surfactant that has multifunctionality. It is formed by the ethoxylation of sorbitol. As the name suggests the ethoxylation process leaves the excipient with 20 repeating units. These repeating units are comprised of polyethylene glycol. Tween 20 has an HLB value of 16.7 meaning it is a hydrophilic surfactant.

Glycerol

In embodiments, the formulations described herein comprise glycerol. Glycerol is a colorless and odorless viscous liquid. It is widely used as a sweetener and humectant in the food and pharmaceutical industry. In embodiments, the formulations comprise from about 5% w/w to about 30% w/w glycerol, for example, about 5% w/w, about 10% w/w, about 15% w/w, about 20% w/w, about 25% w/w, or about 30% w/w glycerol, including all values and ranges there between. In embodiments, the formulations comprise about 20% w/w glycerol.

Xanthan Gum

In embodiments, the formulations described herein comprise xanthan gum. Xanthan gum is commonly used as a food additive and in the pharmaceutical industry as an agent that increases the viscosity of a liquid. In embodiments, the formulations comprise from about 0.01% w/w to about 0.5 w/w xanthan gum, for example, about 0.01% w/w, about 0.05% w/w, about 0.10% w/w, about 0.15% w/w, about 0.20% w/w, about 0.25 w/w, about 0.30% w/w, about 0.35 w/w, about 0.40% w/w, about 0.45 w/w, or about 0.50 w/w xanthan gum, including all values and ranges there between. In embodiments, the formulations comprise about 0.2% w/w xanthan gum.

Antioxidants:

In embodiments, the formulations comprise one or more antioxidants. In embodiments, the antioxidants are selected from the group consisting of butylated hydroxyltoluene; butylated hydroxylanisole; alpha-tocopherol (Vitamin E); ascorbyl palmitate; ascorbic acid; sodium ascorbate; ethylenediamino tetraacetic acid; cysteine hydrochloride; citric acid; sodium citrate; sodium bisulfate; sodium metabisulfite; lecithin; propyl gallate; sodium sulfate; and monothioglycerol. In embodiments, the formulations described herein comprise from about 0.01% w/w to about 50 w/w of an antioxidant, for example, about 0.01% w/w, about 0.02% w/w, about 0.03% w/w, about 0.04% w/w, about 0.05 w/w, about 0.06% w/w, about 0.07% w/w, about 0.08% w/w, about 0.09% w/w, about 0.1% w/w, about 0.2% w/w, about 0.3% w/w, about 0.4% w/w, about 0.5 w/w, about 0.6% w/w, about 0.7% w/w, about 0.8% w/w, about 0.9% w/w, about 1% w/w, about 2% w/w, about 3% w/w, about 4% w/w, about 5% w/w, about 6% w/w, about 7% w/w, about 8% w/w, about 9% w/w, about 10% w/w, about 11 w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25 w/w, about 26% w/w, about 27% w/w, about 28% w/w, about 29% w/w, about 30% w/w, about 31% w/w, about 32% w/w, about 33% w/w, about 34% w/w, about 35 w/w, about 36% w/w, about 37% w/w, about 38% w/w, about 39% w/w, about 40% w/w, about 41% w/w, about 42% w/w, about 43% w/w, about 44% w/w, about 45 w/w, about 46% w/w, about 47% w/w, about 48% w/w, about 49% w/w, or about 50 w/w of an antioxidant. In embodiments, the formulations described herein comprise from about 0.01% w/w to about 2% w/w antioxidant, for example, about 0.01% w/w, about 0.02% w/w, about 0.03% w/w, about 0.04% w/w, about 0.05 w/w, about 0.06% w/w, about 0.07% w/w, about 0.08% w/w, about 0.09% w/w, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1 w/w, or about 2% w/w antioxidant. In embodiments, the formulations described herein comprise about 0.2% w/w antioxidant. In embodiments, the formulations described herein comprise about 0.03% w/w antioxidant. In embodiments, the formulations described herein comprise about 1.2% w/w antioxidant.

Alpha Tocopherol

In embodiments, the antioxidant is alpha tocopherol. Alpha Tocopherol is a derivative if Vitamin E. It is commonly used as an antioxidant in pharmaceutical formulations. In embodiments, the formulations described herein comprise about 0.2% w/w alpha tocopherol. In embodiments, the formulations described herein comprise about 0.03% w/w alpha tocopherol.

Butylated Hydroxytoluene (BHT)

In embodiments, the antioxidant is BHT. BHT is a crystalline antioxidant commonly used in pharmaceutical formulations.

Butylated Hydroxyanisole (BHA)

In embodiments, the antioxidant is BHA. BHA is a crystalline antioxidant commonly used in pharmaceutical formulations.

pH Modulating Agent:

In embodiments, the formulations comprise one or more pH modulating agents. A pH modulating agents is any agent utilized to modulate the pH of a formulation. In embodiments, the pH modulating agent is a buffer.

Sodium Hydroxide

In embodiments, the pH modulating agent is sodium hydroxide. Sodium hydroxide is an alkali commonly used as a pH adjusting agent. In embodiments, the formulations described herein comprise from about 0.1% w/w to about 5% w/w sodium hydroxide, for example, about 0.1%, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.5 w/w, about 2% w/w, about 2.5 w/w, about 3% w/w, about 3.5 w/w, about 4% w/w, about 4.5 w/w, or about 5 w/w sodium hydroxide. In embodiments, the formulations comprise about 1.5% w/w sodium hydroxide.

Phosphate Buffered Saline (PBS)

In embodiments, the pH modulating agent is PBS. PBS is a buffer solution comprising of Sodium chloride, Potassium chloride, Disodium phosphate and Monopotassium phosphate. The pH of PBS is 7.4.

Edetate Calcium Disodium (EDTA)

In embodiments, the formulations comprise a chelating agent. In embodiments, the chelating agent is EDTA. EDTA is a commonly used as chelating agent in pharmaceutical formulations. A chelating agent "mops" up free radicals therefore enhancing the stability of a pharmaceutical formulation.

Solvents:

In embodiments, the formulations comprise one or more pharmaceutically solvents or cosolvents. The terms "solvent" and "cosolvent" are used to refer to the liquid carrier used in formulations comprising the microparticles described herein.

Liquid carriers can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Such pharmaceutically acceptable solvent (or carriers) can be aqueous or non-aqueous solutions, suspensions and emulsions. Examples of non-aqueous carriers include, but are not limited to, propylene glycol, polyethylene glycol, vegetable oils such as olive oil, and injectable organic esters such as ethyl oleate.

Examples of aqueous carriers include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers include, but are not limited to, water (partially containing additives as above, e.g. cellulose derivatives), alcohols (including monohydric alcohols and polyhydric alcohols, e.g. glycols) and their derivatives, and oils (e.g. fractionated coconut oil and *arachis* oil).

In embodiments, water is a cosolvent for formulations comprising a copolymer of methacrylic acid and methyl methacrylate.

In embodiments, acetone is a cosolvent or solvent for formulations comprising HPMCAS.

Cellulose polymers are hard to dissolve to yield solutions, more toxic solvents such as DMSO can dissolve HPMCAS however the trouble comes when having to reduce the solvent concentration to acceptable levels.

Ethanol

In embodiments, ethanol is a cosolvent for formulations comprising a copolymer of methacrylic acid and methyl methacrylate. Ethanol is capable of solubilizes L100 completely but only forms suspensions of S100. Addition of water to a S100 ethanol suspension yields a clear solution.

Extended Release Polymers

The microparticles may also be coated with one or more extended release polymers. Extended release polymers may be combined with the pH-dependent release polymers, or the extended release polymers may be used without the pH-dependent release polymers. When one or more extended release polymers are combined with one or more pH-dependent release polymers, the polymers may be present as a mixture (e.g., in the same layer disposed over the drug or in a matrix), or the polymers may be applied in separate layers.

In embodiments, extended release may be achieved by appropriately coating a drug-containing component with one or more suitable extended release polymers (also referred to as a controlled release polymer or rate-controlling polymer) or embedding the drug in a matrix comprising one or more suitable extended release polymers. In embodiments, the extended release polymer may be a pharmaceutically acceptable water-insoluble polymers (also referred to as hydrophobic polymers), pharmaceutically acceptable water-soluble polymers (also referred to as hydrophilic polymers), pharmaceutically acceptable gastrosoluble polymers, pharmaceutically acceptable enteric polymers (also referred to as pH-dependent release polymers), and combinations thereof.

Non-limiting examples of pharmaceutically acceptable water-insoluble polymers include acrylic polymers, methacrylic acid polymers, acrylic copolymers, such as a methacrylic acid-ethyl acrylate copolymer available under the trade name of EUDRAGIT® (type L, RL, RS and NE30D), and their respective esters, zein, waxes, shellac and hydrogenated vegetable oil, cellulose derivatives, such as ethyl cellulose, cellulose acetate, cellulose acetate butyrate, and the like.

Non-limiting examples of pharmaceutically acceptable water-soluble polymers include homopolymers and copolymers of N-vinyl lactams, including homopolymers and copolymers of N-vinyl pyrrolidone, e.g. polyvinylpyrrolidone (PVP), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, and hydroxypropylmethylcellulose, cellulose phthalates, succinates, butyrates, or trimellitates, in particular cellulose acetate phthalate, hydroxypropylmethylcellulose phthalate, hydroxypropylmethylcellulose succinate, and hydroxypropylmethylcellulose acetate succinate; high molecular polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, polyethylene glycol oligo- and polysaccharides such as carrageenans, galactomannans and xanthan gum, or mixtures of one or more thereof.

Non-limiting examples of gastrosoluble polymers include maltrin, an aminoalkyl methacrylate copolymer available under the trade name of EUDRAGIT® (type E100 or EPO), polyvinylacetal diethylaminoacetate e.g., AEA® available from Sankyo Company Limited, Tokyo (Japan), and the like.

Non-limiting examples of such enteric polymers include carboxymethylethylcellulose, cellulose acetate phthalate (CAP), cellulose acetate succinate, methylcellulose phthalate, hydroxy methyl ethylcellulose phthalate, hydroxypropylmethylcellulose phthalate (HPMCP), hydroxypropylmethylcellulose acetate succinate (HPMCAS), polyvinyl alcohol phthalate, polyvinyl butyrate phthalate, polyvinyl acetal phthalate (PVAP), a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, cellulose acetate hexahydrophthalate, hydroxypropyl methylcellulose hexahydrophthalate, hydroxypropyl methylcellulose phthalate, cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT L), methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC, copal collophorium, and combinations comprising one or more of the foregoing polymers. Yet other examples of enteric polymers include synthetic resin bearing carboxyl groups. The term "enteric polymer" as used herein is defined to mean a polymeric substance that when used in an enteric coat formulation, is substantially insoluble and/or substantially stable under acidic conditions at a pH of less than about 5 and which are substantially soluble or can decompose under conditions exhibiting a pH of about 5 or more.

Non-limiting examples of hydrophilic polymers include hydroxypropyl celluloses (HPC), hydroxypropyl methylcelluloses, methylcelluloses, polyethylene oxides, sodium carboxymethyl celluloses, and the like, or combinations thereof.

In some embodiments, the delayed release coating may comprise about 10 wt % to about 95 wt % of any of pharmaceutically acceptable polymers listed above (e.g., about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%, inclusive of all values and subranges therebetween) and about 5 wt % to about 60 wt % plasticizer (e.g., about 10%, about 15%, about 20%, about 25%, about 30%, about 35%, about 40%, about 45%, about 50%, about 55%, inclusive of all values and subranges therebetween) based on the total weight of the polymer coating. The relative proportions of ingredients, notably the ratio of the enteric polymer to plasticizer can be varied according to methods known to those of skill in the art of pharmaceutical formulation.

Formulations and Methods of Manufacture

The microparticulates described herein may be formulated in any suitable formulation. In some embodiments, the formulation may be, but not limited to, an oral solution, an oral suspension, a formulation comprising granules, a formulation comprising sprinkles to be mixed with food, a compressed tablet, a mucoadhesive gel, a tablet, a powder, a liquid gel capsule, a solid powder filled capsule, an extrudate, a nasal spray or an injectable formulation.

In embodiments, the pharmaceutical compositions of the present disclosure, comprise at least one pharmaceutically acceptable carrier, diluent, and/or excipient. Pharmaceutically acceptable carriers, diluents or excipients include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier.

Suitable pharmaceutically acceptable carriers include, but are not limited to, inert solid fillers or diluents and sterile aqueous or organic solutions. Pharmaceutically acceptable carriers for liquid compositions are well known to those skilled in the art and include, but are not limited to, aqueous and non-aqueous solutions. Pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate. Aqueous carriers suitable for use in the present application include, but are not limited to, water, ethanol, alcoholic/aqueous solutions, glycerol, emulsions or suspensions, including saline and buffered media.

Liquid carriers suitable for use in the present application include, but are not limited to, water, alcohols (including monohydric alcohols and polyhydric alcohols, e.g. glycols) and their derivatives, and oils (e.g. fractionated coconut oil and *arachis* oil).

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Solid carriers suitable for use in the present application include, but are not limited to, inactive substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets may contain up to 99% of the active compound. Suitable solid carriers include, for example, calcium phosphate, magnesium stearate, talc, sugars, lactose, dextrin, starch, gelatin, cellulose, polyvinylpyrrolidone, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally coated or scored and may be formulated so as to provide delayed of the active ingredient therein using, for example, one or more pH dependent release polymers described herein in varying proportions to provide the desired release profile. Tablets provided with a coating comprising a pH dependent release polymer provide releases in parts of the gut other than the stomach.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations described herein. Diluents increase the bulk of a solid pharmaceutical composition and/or combination, and may make a pharmaceutical dosage form containing the composition and/or combination easier for the patient and care giver to handle. In various embodiments, diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc, and/or mixtures of any of the foregoing. Specific examples of: microcrystalline cellulose include those sold under the Trademark Avicel (FMC Corp., Philadelphia, Pa.), for example, Avicel™ pH101, Avicel™ pH102 and Avicel™ pH112; lactose include lactose monohydrate, lactose anhydrous and Pharmatose DCL21; dibasic calcium phosphate includes Emcompress.

Lubricants are used to facilitate tablet manufacture, promoting powder flow and preventing particle capping (i.e., particle breakage) when pressure is relieved. Useful lubricants include, but are not limited to, magnesium stearate, calcium stearate, stearic acid, glyceryl behenate, talc, colloidal silicon dioxide such as Aerosil™ 200, mineral oil (in PEG), hydrogenated vegetable oil (e.g., comprised of hydrogenated and refined triglycerides of stearic and palmitic acids), and combinations thereof.

Binders are used to impart cohesive qualities to a tablet, and thus ensure that the tablet or tablet layer remains intact after compression. Suitable binder materials include, but are not limited to, starch (including corn starch and pregelatinized starch), gelatin, sugars (including sucrose, glucose, dextrose and lactose), polyethylene glycol, polyvinyl alcohol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum, and combinations thereof. Examples of polyvinylpyrrolidone include povidone, copovidone and crospovidone.

Fillers include, for example, materials such as silicon dioxide, titanium dioxide, alumina, talc, kaolin, powdered cellulose, microcrystalline cellulose, urea, sodium chloride, as well as saccharides, or combinations thereof. Any suitable saccharide may be used in the composition of the present invention. As used herein, the "saccharides" used in the invention include sugar alcohols, monosaccharides, disaccharides, and oligosaccharides. Exemplary sugar alcohols include, but not limited to, xylitol, mannitol, sorbitol, erythritol, lactitol, pentitol, and hexitol. Exemplary monosaccharides include, but are not limited to, glucose, fructose, aldose and ketose. Exemplary disaccharides include, but are not limited to, sucrose, isomalt, lactose, trehalose, and maltose. Exemplary oligosaccharides include, but are not limited to, fructo-oligosaccharides, inulin, galacto-ologosaccharides, and mannan-oligosaccharides. In some embodiments, the saccharide is sorbitol, mannitol, or xylitol. In some embodiments, the saccharide is sorbitol. In some embodiments, the saccharide is sucrose.

Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Other non-limiting examples of suitable disintegrants include, for example, lightly crosslinked polyvinyl pyrrolidone, corn starch, potato starch, maize starch and modified starches, croscarmellose sodium, crospovidone, sodium starch glycolate, and combinations and mixtures thereof.

The cannabinoid-containing microparticulate may be formulated in any suitable form in which the pH dependent release polymer(s) substantially prevents release of cannabinoid in the acidic environment of the stomach, such as, but not limited to, drug-coated core particles, solid blends comprising the drug, mini-tablets, microcapsules, pellets, microspheres, microemulsion, and matrices. In embodiments, the microparticulate is in the form of particles that contain the cannabinoid layered on the core.

The core may comprise different oxides, celluloses, organic polymers and other materials, alone or in mixtures, or water soluble seeds comprising different inorganic salts, sugars, nonpareil cores and other materials, alone or in mixtures. In embodiments, the core may be a sphere comprising sugar, microcrystalline cellulose (MCC), polyol, carnauba wax, silica, lactose-starch, or lactose-cellulose. In embodiments, the core may be a buffer crystal or an encapsulated buffer crystal, such as calcium carbonate, sodium bicarbonate, fumaric acid, tartaric acid, etc. Buffer crystals are useful to alter the microenvironment.

In embodiments, the microparticles may be prepared by rotogranulation, high-shear granulation, spray congealing, extrusion-spheronization and/or compression of the cannabinoid, and one or more excipients described herein (e.g., pH dependent release polymer).

The pH dependent release polymer may be applied by spraying a solution containing the component (e.g., dispersing or solution containing the drug or enteric polymer) using e.g., a fluid bed coater.

In embodiments, the microparticulate is in the form of a matrix. A matrix refers to a composition in which the cannabinoid is distributed or dispersed in one or more pH dependent release polymers.

The size of the microparticles of the disclosure may be selected to improve palatability. Large particles can have a gritty or rough feeling, while smaller particles were discovered to have improved organoleptic properties. In some embodiments, the microparticles of the present disclosure have a particle size less than about 300 µm, e.g., less than about 250 µm, less than 200 µm, e.g., about 200 µm, about 150 µm, about 100 µm, or about 50 µm or less, including all values ranges in between. In some embodiments, the microparticles described herein have a particle size from about 1 µm to about 200 µm, about 1 µm to about 100 µm, about 1 µm to about 50 µm, about 1 µm to about 25 µm, or from about 5 µm to about 10 µm including all values ranges in between. In some embodiments, the microparticles described herein have a particle size from about 5 µm to about 10 µm The pharmaceutical formulation of the present invention may be prepared by any well-known methods in the art, such as mixing, spray-drying, dissolving, granulating, dragee-making, levigating, emulsifying, encapsulating, entrapping, fluid-bed coating, or lyophilizing processes. As mentioned above, the compositions of the present disclosure may include one or more pharmaceutically acceptable carriers such as excipients and adjuvants that facilitate processing of active molecules into preparations for pharmaceutical use.

Pharmaceutical compositions for oral use may be obtained as solid excipients, optionally grinding a resulting mixture, and processing the mixture of granules, after adding suitable adjuvants, if desired, to obtain tablets or dragee cores. Such oral pharmaceutical compositions may also be prepared by milling or melt extrusion. Suitable excipients may be any of those disclosed herein and, in particular, fillers such as sugars, including lactose, sucrose, mannitol, or sorbitol; cellulose formulation such as maize starch, wheat starch, rice starch, potato starch, gelatin, gum tragacanth, methyl cellulose, hydroxypropyl methylcellulose, sodium carboxymethylcellulose, and/or polyvinylpyrrolidone (PVP) formulation. Also, disintegrating agents may be employed, such as cross-linked polyvinylpyrrolidone, agar, or alginic acid or a salt thereof such as sodium alginate. Wetting agents, such as sodium dodecyl sulfate and the like, may be added.

Different forms of administration may be utilized to deliver the formulations described herein, including (but not limited to) oral, parenteral, inhalation topical. The term parenteral as used here includes subcutaneous, intravenous, intramuscular, and intraarterial injections with a variety of infusion techniques.

Dissolution Profile

The pH dependent release polymers prevent release of the cannabinoid (or cannabinoids) in the acidic environment of the stomach, and enable release in the pH of the lower intestines (after the drug traverse the stomach) or the colon. In the intestines is roughly pH 6, the colon is roughly pH 7.

In embodiments, drug release is measured as described in Example 2.

The USP 711 Dissolution test may be used to measure the dissolution (release) of the cannabinoid from the microparticle under different conditions. Examples of such tests include USP Apparatus 1 (basket) or 2 (paddle). The USP 711 Dissolution test is described in, e.g., The United States Pharmacopeial Convention, 2011. For example, the USP Apparatus 1 uses the following 2-stage buffer conditions: Paddle, 100 RPM, Stage-1: 750 mL 0.1N HCl (2 h) and equilibrate to 37±0.5° C.; Stage-2: Add 250 mL of 0.2 M tribasic sodium phosphate to make pH 6.8 (30 minute) and equilibrate to 37±0.5° C.

In embodiments, the microparticles and formulations described herein display minimal (e.g., less than 10% or less than 5%) in the acid phase (e.g., HCl 0.1N) of the USP test but release occurs in the buffer phase (pH=6.8) of the USP test. Release in the buffer phase may be greater than about 90% (e.g. about 91%, about 92%, about 93%, about 94%, about 95%, about 96%, about 97%, about 98%, about 99%, or about 100%). In embodiments, release is measured within about 30 minutes, about 40 minutes, about 50 minutes, 1 hour, about 1.1 hours, about 1.2 hours, about 1.3 hours, about 1.4 hours, 1.5 hours, about 1.6 hours, about 1.7 hours, about 1.8 hours, about 1.9 hours, 2 hours, about 2.1 hours, about 2.2 hours, about 2.3 hours, about 2.4 hours, 2.5 hours, about 2.6 hours, about 2.7 hours, about 2.8 hours, about 2.9 hours, 3 hour, or more.

In embodiments, substantially no drug (e.g., less than 10%, or less than 5%) is released within about 30 minutes, about 45 minutes, about 50 minutes, about 1 hour, about 1.1 hours, about 1.2 hours, about 1.3 hours, about 1.4 hours, 1.5 hours, about 1.6 hours, about 1.7 hours, about 1.8 hours, about 1.9 hours, 2 hours, about 2.1 hours, about 2.2 hours, about 2.3 hours, about 2.4 hours, 2.5 hours, about 2.6 hours, about 2.7 hours, about 2.8 hours, about 2.9 hours, 3 hour, or more.

In embodiments, after the initial delay period in which substantially no drug is released, the remainder of the drug is released within about 30 minutes, about 45 minutes, about 50 minutes, about 1 hour, about 1.1 hours, about 1.2 hours, about 1.3 hours, about 1.4 hours, 1.5 hours, about 1.6 hours, about 1.7 hours, about 1.8 hours, about 1.9 hours, 2 hours, about 2.1 hours, about 2.2 hours, about 2.3 hours, about 2.4 hours, 2.5 hours, about 2.6 hours, about 2.7 hours, about 2.8 hours, about 2.9 hours, 3 hours, about 3.1 hours, about 3.2 hours, about 3.3 hours, about 3.4 hours, 3.5 hours, about 3.6 hours, about 3.7 hours, about 3.8 hours, about 3.9 hours, 4 hours, about 4.1 hours, about 4.2 hours, about 4.3 hours, about 4.4 hours, 4.5 hours, about 4.6 hours, about 4.7 hours, about 4.8 hours, about 4.9 hours, 5 hours, about 5.1 hours, about 5.2 hours, about 5.3 hours, about 5.4 hours, 5.5 hours, about 5.6 hours, about 5.7 hours, about 5.8 hours, about 5.9 hours, 6 hours, about 6.1 hours, about 6.2 hours, about 6.3 hours, about 6.4 hours, 6.5 hours, about 6.6 hours, about 6.7 hours, about 6.8 hours, about 6.9 hours, 7 hours, or more.

EMBODIMENTS

Embodiment 1. A microparticulate cannabinoid containing formulation comprising one or more cannabinoids and a pH dependent release polymer.

Embodiment 2. A microparticulate cannabinoid containing formulation according to embodiment 1, wherein the one or more cannabinoids are taken from the group consisting of: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA).

Embodiment 3. A microparticulate cannabinoid containing formulation according to embodiment 1, wherein the pH dependent release polymer is taken from the group consisting of: a copolymer of methacrylic acid and methacrylate, a copolymer of methacrylic acid and methyl methacrylate (Eudragit), a copolymer of methacrylic acid and ethylacrylate, hydroxypropyl methyl cellulose acetate succinate (HPMCAS), hydroxypropyl methyl cellulose phthalate (HPMCP), polyvinyl acetate phthalate (PVAP), a copolymer of methyl vinyl ether and maleic anhydride, cellulose acetate phthalate (CAP), cellulose acetate butyrate (CAB), cellulose acetate trimellitate (CAT), cellulose acetate succinate (CAS), ethyl cellulose, methyl cellulose, shellac, gellan gum, zein, alginic acid and waxes.

Embodiment 4. A microparticulate cannabinoid containing formulation according to embodiment 3, wherein the pH dependent release polymer is HPMCAS or Eudragit.

Embodiment 5. A microparticulate cannabinoid containing formulation according to embodiment 4, wherein the pH dependent release polymer is taken from the group consisting of: HPMCAS-L; HPMCAS-M; HPMCAS-H; Eudragit S100; Eudragit L100.

Embodiment 6. A microparticulate cannabinoid containing formulation according to any of preceding claims, further comprising one or more wetting agents.

Embodiment 7. A microparticulate cannabinoid containing formulation according to embodiment 6, wherein the one or more wetting agents are taken from the group consisting of: poloxamers; poloxamer 188; and sodium carbonate.

Embodiment 8. A microparticulate cannabinoid containing formulation according to any of preceding embodiment, further comprising one or more suspending agents.

Embodiment 9. A microparticulate cannabinoid containing formulation according to embodiment 8, wherein the one or more suspending agents are taken from the group consisting of: polysorbate 20; glycerol; and xanthan gum.

Embodiment 10. A microparticulate cannabinoid containing formulation according to any of the preceding embodiment, further comprising one or more pH buffers.

Embodiment 11. A microparticulate cannabinoid containing formulation according to claim 10, wherein the one or more pH buffers are taken from the group consisting of: citric acid; sodium phosphate dibasic; sodium hydroxide; and phosphate buffered saline.

Embodiment 12. A microparticulate cannabinoid containing formulation according to any of the preceding embodiment, further comprising one or more preservatives.

Embodiment 13. A microparticulate cannabinoid containing formulation according to embodiment 12, wherein the one or more preservatives are taken from the group consisting of: potassium sorbate; and sodium benzoate.

Embodiment 14. A microparticulate cannabinoid containing formulation according to any of the preceding embodiments, further comprising one or more antioxidants.

Embodiment 15. A microparticulate cannabinoid containing formulation according to embodiments 14, wherein the one or more antioxidants are taken from the group consisting of: butylated hydroxyltoluene; butylated hydroxylanisole; alpha-tocopherol (Vitamin E); ascorbyl palmitate; ascorbic acid; sodium ascorbate; ethylenediamino tetraacetic acid; cysteine hydrochloride; citric acid; sodium citrate; sodium bisulfate; sodium metabisulfite; lecithin; propyl gallate; sodium sulfate; monothioglycerol and mixtures thereof.

Embodiment 16. A microparticulate cannabinoid containing formulation according to any of the preceding embodiments, further comprising one or more solvents.

Embodiment 17. A microparticulate cannabinoid containing formulation according to embodiment 16, wherein the one or more solvents is taken from the group consisting of: water; ethanol and acetone.

Embodiment 18. A microparticulate cannabinoid containing formulation according to any of the preceding embodiments, wherein the one or more cannabinoids are present in an amount of from about 10 to 50 wt %, based on the pharmaceutical formulation, preferably from about 10 to 30 wt %, more preferably from about 20 to 30 wt %.

Embodiment 19. A microparticulate cannabinoid containing formulation according to any of the preceding embodiments, wherein the formulation is an oral dosage form selected from the group consisting of: a mucoadhesive gel;

a tablet; a powder; a liquid gel capsule; a solid capsule; an oral solution; an oral suspension; a granulate; and an extrudate.

Embodiment 20. A microparticulate cannabinoid containing formulation according to any of the preceding embodiments, for use in the treatment of conditions requiring the administration of a neuroprotectant or anti-convulsive medication.

Embodiment 21. A microparticulate cannabinoid containing formulation for use according to embodiment 20, for use in the treatment of seizures.

Embodiment 22. A microparticulate cannabinoid containing formulation for use according to embodiment 20, for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, *cannabis* use disorder, post-traumatic stress disorder, anxiety, early psychosis, Alzheimer's disease, and autism.

Embodiment 23. A method of preparing a microparticulate cannabinoid containing formulation according to any of the preceding embodiments, comprising spray drying the formulation.

Embodiment 24. A method of preparing a microparticulate cannabinoid containing formulation according to any of the preceding embodiments, comprising:

1. Preparing a mixture of the cannabinoid and pH dependent release polymer;
2. Producing an intermediate powder blend;
3. Processing the intermediate powder blend through a hot melt extruder
4. Pelleting the extrudates; and
5. Milling the pellets to 250-500 μm.

Embodiment 25. A method according to embodiment 24, wherein an antioxidant is added after step (i).

Embodiment 26. A method according to embodiment 24, wherein a disintegrant is added after step (i).

Embodiment 27. A method of treating a subject comprising administering a microparticulate cannabinoid containing formulation according to any of claims 1 to 19 to the subject.

Embodiment 29. A method according to embodiment 27, wherein the subject is a human.

Embodiment 30. The microparticulate or unit dose according to any of the preceding embodiments, wherein the microparticulate or unit dose is formulated as a mucoadhesive gel; a tablet; a powder; a liquid gel capsule; a solid capsule; an oral solution; an oral suspension; a granulate; an extrudate; or a sprinkle.

Example 1: Formulations

In embodiments, the microparticulate cannabinoid formulation according to the invention is able to minimize cannabinoid metabolism.

Polymeric microspheres have the potential to reduce the metabolism via two different mechanisms. First, microparticles with a size ranging from 5-10 μM can be engulfed as a whole particle by the intestinal cell wall therefore protecting the entrapped drug from degradative enzymes.

Secondly controlled release polymers can be used to deliver the entrapped drug to different parts of the GI tract such as the colon; this turn may alter the metabolic profile of the entrapped cannabinoid.

The following are representative cannabinoid microspheres. Here the active agent is provided as cannabidiol, however the microspheres may be produced using any natural or synthetic cannabinoid, their salts or prodrugs.

| 120% CBD HPMCAS-L 5% P188 Microspheres | |
|---|---|
| CBD | 20 (% w/w) |
| HPMCAS-L | 74.8 (% w/w) |
| Kolliphor P188 | 5 (% w/w) |
| Alpha Tocopherol | 0.2 (% w/w) |

| 15% HPMCAS-M 5% P188 Microspheres | |
|---|---|
| CBD | 15 (% w/w) |
| HPMCAS-M | 79.8 (% w/w) |
| Kolliphor P188 | 5 (% w/w) |
| Alpha Tocopherol | 0.2 (% w/w) |

| 20% CBD L100 Microspheres | |
|---|---|
| CBD | 20 (% w/w) |
| Eudragit L100 | 78.28 (% w/w) |
| Calcium Disodium EDTA | 1.52 (% w/w) |
| Alpha Tocopherol | 0.2 (% w/w) |

| 15% CBD S100 5% P188 Microspheres | |
|---|---|
| CBD | 15 (% w/w) |
| Eudragit L100 | 78.28 (% w/w) |
| Kolliphor P188 | 5 (% w/w) |
| Sodium Hydroxide | 1.52 (% w/w) |
| Alpha Tocopherol | 0.2 (% w/w) |

| 15% CBD S100 20% P188 Microspheres | |
|---|---|
| CBD | 15 (% w/w) |
| Eudragit L100 | 63.28 (% w/w) |
| Kolliphor P188 | 20 (% w/w) |
| Sodium Hydroxide | 1.52 (% w/w) |
| Alpha Tocopherol | 0.2 (% w/w) |

As is described above, the cannabinoid was added at a concentration of 15% and 20% to produce the microspheres, however concentrations may be used of from 0.1% to 30% cannabinoid. The concentration of the cannabinoid will depend on the cannabinoid used and the therapeutic indication for which the microsphere is to be used to treat.

Tables 2 to 6 below illustrate example formulations suitable for colonic or enteric release. Here the cannabinoid microspheres described above have been formulated to produce a suspension. The cannabinoids used in these example formulations are cannabidiol (CBD) or a combination of highly purified CBD and a CBD BDS, here there is a mixture of major cannabinoids in the formulation, namely CBD and THC in addition to the other minor cannabinoids and non-cannabinoids which occur in a BDS. Clearly other cannabinoids or combinations of purified and BDS can be utilized to prepare colonic or enteric release formulations.

TABLE 2

Example formulation for 30 mg/mL CBD Enteric Release (ER) suspension

| Component | Composition (% w/w) | Compositions (mg/mL) |
|---|---|---|
| Cannabidiol (CBD) | 3 | 30.00 |
| AQOAT HPMCAS-L | 11.22 | 112.20 |
| Kolliphor P188 | 0.75 | 7.50 |
| Alpha-Tocopherol | 0.03 | 0.30 |
| Glycerol | 20 | 200.00 |
| Xanthan Gum | 0.2 | 2.00 |
| Citric Acid | 0.25 | 2.50 |
| Sodium Phosphate Dibasic | 0.12 | 1.20 |
| Potassium Sorbate | 0.10 | 1.00 |
| Sodium Benzoate | 0.10 | 1.00 |
| Ascorbic Acid | 0.20 | 2.00 |
| Water | Q.S to 100% | Q.S. to 100% |

TABLE 3

Example formulation for 25 mg/mL CBD Colonic Release (CR) suspension 5% P188

| Component | Composition (% w/w) | Compositions (mg/mL) |
|---|---|---|
| Cannabidiol (CBD) | 2.50 | 25.00 |
| Eudragit S100 | 13.00 | 130.00 |
| Kolliphor P188 | 0.75 | 7.50 |
| Alpha-Tocopherol | 0.03 | 0.30 |
| Sodium Hydroxide | 0.25 | 2.50 |
| Glycerol | 20.00 | 200.00 |
| Xanthan Gum | 0.20 | 2.00 |
| Citric Acid | 1 | 10.00 |
| Sodium Phosphate Dibasic | 0.48 | 4.80 |
| Potassium Sorbate | 0.10 | 1.00 |
| Sodium Benzoate | 0.10 | 1.00 |
| Ascorbic Acid | 0.20 | 2.00 |
| Water | Q.S to 100% | Q.S. to 100% |

TABLE 4

Example formulation for 25 mg/mL CBD Colonic Release (CR) suspension 20% P188

| Component | Composition (% w/w) | Compositions (mg/mL) |
|---|---|---|
| Cannabidiol (CBD) | 2.50 | 25.00 |
| Eudragit S100 | 10.75 | 107.50 |
| Kolliphor P188 | 3 | 30 |
| Alpha-Tocopherol | 0.03 | 0.30 |
| Sodium Hydroxide | 0.25 | 2.50 |
| Glycerol | 20.00 | 200.00 |
| Xanthan Gum | 0.20 | 2.00 |
| Citric Acid | 1 | 10.00 |
| Sodium Phosphate Dibasic | 0.48 | 4.80 |
| Potassium Sorbate | 0.10 | 1.00 |
| Sodium Benzoate | 0.10 | 1.00 |
| Ascorbic Acid | 0.20 | 2.00 |
| Water | Q.S to 100% | Q.S. to 100% |

TABLE 5

Example formulation for 24 mg/mL CBD 0.6 mg/mL THC Enteric Release (ER) suspension

| Component | Composition (% w/w) | Compositions (mg/mL) |
|---|---|---|
| CBD Pure | 1 | 10.00 |
| CBD BDS | 2 | 20.00 |
| AQOAT HPMCAS-L | 11.22 | 112.2 |
| Kolliphor P188 | 0.75 | 7.50 |
| Alpha-Tocopherol | 0.03 | 0.30 |
| Glycerol | 20 | 200.00 |
| Xanthan Gum | 0.2 | 2.00 |
| Citric Acid | 0.25 | 2.50 |
| Sodium Phosphate Dibasic | 0.12 | 1.20 |
| Potassium Sorbate | 0.10 | 1.00 |
| Sodium Benzoate | 0.10 | 1.00 |
| Ascorbic Acid | 0.20 | 2.00 |
| Water | Q.S to 100% | Q.S to 100% |

TABLE 6

Example formulation for 20 mg/mL CBD 0.5 mg/mL THC Colonic Release (CR) suspension

| Component | Composition (% w/w) | Compositions (mg/mL) |
|---|---|---|
| CBD Pure | 0.825 | 8.25 |
| CBD BDS | 1.665 | 16.67 |
| Eudragit S100 | 13.00 | 130.00 |
| Kolliphor P188 | 0.75 | 7.50 |
| Alpha-Tocopherol | 0.03 | 0.30 |
| Sodium Hydroxide | 0.25 | 2.5 |
| Glycerol | 20.00 | 200.00 |
| Xanthan Gum | 0.20 | 2.00 |
| Citric Acid | 1 | 10.00 |
| Sodium Phosphate Dibasic | 0.48 | 4.80 |
| Potassium Sorbate | 0.10 | 1 |
| Sodium Benzoate | 0.10 | 1 |
| Ascorbic Acid | 0.20 | 2 |
| Water | Q.S to 100% | Q.S. to 100% |

Method of Administration

The formulations as described above in Tables 2 to 5 are suitable for administration as a medicament. The medicament may be an oral solution, an oral suspension, a formulation comprising granules, a formulation comprising sprinkles to be mixed with food, a compressed tablet, a mucoadhesive gel, a tablet, a powder, a liquid gel capsule, a solid powder filled capsule, an extrudate, a nasal spray or an injectable formulation. Different forms of administration may be utilized, including (but not limited to) oral, parenteral, inhalation topical.

When provided as a suspension or an oral solution, the formulation may be dispensed in bottles optionally with syringes such that an accurate dose may be provided to the patient based on an amount of cannabinoid (in mg) per weight of patient (in kg).

In addition, the formulation may be prepared in alternative means such as a spray, a drink or in a small volume such as 30 mL of solution that is administered to the patient before swallowing.

The Examples that follow describe the development of the formulations comprising cannabinoid microspheres. Such formulations are designed to release their active agent in either the intestines (enteric) or in the colon. Enteric or colonic delivery of cannabinoids which are known to undergo rapid metabolism to inactive metabolites in the body provides a surprisingly efficient way of drug delivery.

Example 2: Selection of Excipients to Produce an Enteric-Release and a Colonic-Release Microparticulate Formulation Drug Hydration Studies In vitro experimentation assessing drug release from a polymer matrix is important to ensure drug release is achieved from a microparticle in vivo.

Polymer films comprising of API, polymer and wetting agents (if applicable) were manufactured using a solvent casting method.

The produced films were then hydrated in a pH 7.0 buffer and drug release from the polymer films was assessed.

Five different polymers were assessed during drug hydration: Eudragit L100; Eudragit S100; HPMCAS-L; HPMCAS-M and HPMCAS-H.

Two different wetting agents, Poloxamer 188 and Tween 20 were also assessed.

Results of experimentation indicated that a wetting agent is required to aid drug release for all polymers except for the Eudragit L100 polymer. Additionally, it was found that Poloxamer 188 is a more effective wetting agent than Tween 20.

Once hydrated the films formed turbid emulsion. The drug release from the HPMCAS-H polymer was poor at differing drug and wetting agent concentrations.

The following drug and wetting agent concentrations were decided upon and taken forward for further development:

20% CBD; HPMCAS-L; 5% P188
15% CBD; HPMCAS-M; 5% P188
20% CBD; Eudragit L100
15% CBD; Eudragit 5100; 20% P188

With the inclusion of wetting agent into the polymer matrices for 3 of the 4 polymers there is a risk that drug release may occur at a pH value consistent with stomach pH. The pH of the stomach is approximately 4.0.

Therefore, films at the above drug and wetting agent concentrations were tested for hydration in a buffer with a pH of 4.0. Drug release, as measured under USP 711, at this pH was less than 0.5% for all of the polymer systems tested showing that the inclusion of P188 as a wetting agent did not modify the pH at which the polymer matrix should release the drug as is shown in Table 7 below.

TABLE 7

Percentage drug release at intended and gastric pH

| Formulation | % Drug release at intended pH | % Drug release at gastric pH |
| --- | --- | --- |
| 20% CBD; HPMCAS-L; 5% P188 | 96 | 0 |
| 15% CBD; HPMCAS-M; 5% P188 | 93 | 0 |
| 20% CBD; Eudragit L100 | 96 | 0.3 |
| 20% CBD; Eudragit S100; 20% P188 | 95 | 0 |

Antioxidant Screening

It was necessary to include an antioxidant into the CBD/Polymer system as it was observed that the cannabinoid CBE-I was being formed. CBE I is an oxidation derived degradant of CBD which in turn further degrades to CBE II.

3 different antioxidants were screened, all at a concentration of 0.2% w/w:
Alpha-Tocopherol
Butylated Hydroxytoluene
Butylated Hydroxyanisole These were included in 4 different polymer matrices each with a nominal CBD drug loading of 15%:
HPMCAS-L
HPMCAS-M
Eudragit L100
Eudragit S100

Samples were manufactured and stored at 40° C./75% RH for a period of 28 days.

Results indicated that for both HPMCAS-L and HPMCAS-M an antioxidant is required as the addition of antioxidant also significantly reduced the number of unknown degradants that were formed in the samples.

The samples containing Eudragit L100 and Eudragit S100 behaved differently than the HPMCAS based samples. The addition of the antioxidant reduced the levels of CBE I and CBE II to below the level of quantification over the course of the study, however large quantities of THC were seen in the samples regardless of whether or not an antioxidant was present. The antioxidant had no effect on the formation of THC. This is because the degradation of CBD to THC is an acidic mechanism and not an oxidation mechanism.

From these experiments it was concluded that all four polymer systems would benefit from the addition of an antioxidant.

Example 3: Method of Manufacture for an Enteric-Release and a Colonic-Release Microparticulate Formulation Two alternative methods of manufacture for an enteric-release and a colonic-release microparticulate formulation have been developed. Firstly, spray drying which provides a fine powder which can be further formulated into a suspension or tablet and secondly a hot melt extrusion process whereby a granulate is produced which may be used as an additive or sprinkle. The two processes are described in further detail below.

Spray Drying

It was determined whether it was possible to spray dry formulations comprising HPMCAS-L (Table 2) and Eudragit S100 (Table 4) containing CBD to form dry powders. Both polymers were spray dried with a nominal drug concentration of 15%.

The HPMCAS-L was spray dried with CBD using the following conditions:
Drug concentration: 15%
Solid concentration: 5%
Inlet temperature: 85° C.
Outlet temperature: 55° C.
Aspirator: 75%
Pump: 5%
Solvent: Acetone The Eudragit S100 was spray dried with CBD using the following conditions:
Drug concentration: 15%
Solid concentration: 3%
Inlet temperature: 100° C.
Outlet temperature: 62° C.
Aspirator: 100%
Pump: 5%
Solvent: Ethanol:Water 50:50 ratio.

The above conditions produced spray dried powders for both polymers tested showing it is possible to create spray dried powders comprising of HPMCAS and CBD and Eudragit S100 and CBD.

Because of the chemical similarities between the different grades on HPMCAS a positive result for HPMCAS-L would indicate a positive result for the other grades. Eudragit S100 and Eudragit L100 also share similar chemical structures which would indicate that spray drying CBD with L100 would give a positive result.

The following configuration spray dryer is preferred:
Two fluid nozzles with 0.7 mm nozzle tip
Drying gas: Nitrogen
Negative pressure mode
Use of High-performance cyclone instead of standard cyclone
Long drying chamber used with waste collection attachment HPMCAS Polymers Spray drying of HPMCAS-L and HPMCAS-M was interchangeable and as such the same process could be used for HPMCAS-L and HPMCAS-M.

Acetone was chosen as the solvent for spray drying due to its ability to solubilise cannabinoids and HPMCAS. Additionally, it is an FDA Class III solvent because of its limited toxicity. In Acetone HPMCAS dissolves to yield a fine suspension.

Eudragit Polymers

A mixture of Ethanol and 0.5% w/w EDTA solution was chosen as the solvent mix for the spray drying of the Eudragit L100 polymer. Ethanol was chosen as it is a suitable solvent for cannabinoids and Eudragit L100. It is also an FDA Class III solvent because of its limited toxicity. The EDTA was required as it helped to stabilise the final CBD L100 polymer system. The Ethanol and EDTA solution were completely miscible. The solvent mix comprised of an 80:20 ratio of Ethanol to EDTA solution. Further optimisation could be performed to increase the Ethanol content further, a higher Ethanol content is advantageous because it is more volatile than water A mixture of Ethanol and 0.1M Sodium hydroxide was chosen as the solvent mix for the spray drying of the Eudragit S100 polymer for the reasons stated above. 0.1M NaOH was the stabiliser of choice for the S100 polymer system.

Application of Spray Dried Formulation

The resulting spray dried powder generated in the experiments above can then be further formulated to provide a pharmaceutically acceptable formulation.

The spray dried powder may be mixed with a solvent such as water or glycerol to produce a suspension which may be administered orally as a solution. The spray dried powder may alternatively be compressed into tablets of filled in capsules to be swallowed by a patient.

Hot Melt Extrusion

An alternative means of administration of the microparticulate formulation of the invention is provided. Using the technique of holt melt extrusion a microparticulate granule is produced. Such granules may be used as an additive to food as a sprinkle. Such dosage options are of benefit to younger patients and those patients that may have difficulty swallowing a tablet.

Hot melt extrusion is a process which uses heat and pressure to melt the polymer and active agent. It is solvent free and may increase the solubility and bioavailability of an active agent.

The process is as follows:

The polymer and cannabinoid are mixed together. Optionally an antioxidant and/or a distintegrant may be added after this stage. The blend is mixed to form an intermediate powder blend which is then processed through the hot melt extruder. The extrudates are then pelletised and further milled to the required size. A pellet size of 500 µm/250 µm is preferred.

Samples of hot melt extrusion produced sprinkles were tested to determine they would release at their intended pH rather than at gastric pH and all formulations tested released ranging from 93-96% of their active at the intended pH. None released any active at gastric pH.

The stability of the hot melt extruded polymers was tested over a 12 week period and there were no significant increase of CBD related degradants over the time period nor any changes in the particle size.

Example 4: Stability of an Enteric-Release and a Colonic-Release Microparticulate Formulation Two different formulations prepared by spray drying and further formulating into a suspension were put into a short-term stability study as described in Table 8 below.

TABLE 8

Formulation and storage conditions for stability testing

| Number | Formulation with microparticulates containing: | Time points (days) | Storage conditions |
| --- | --- | --- | --- |
| 1 | 30 mg/mL CBD; HPMCAS-L | 0, 7, 21, 42 | 5° C./25° C./30° C. |
| 2 | 25 mg/mL CBD; Eudragit S100, 20% P188 | 0, 7, 21, 42 | 25° C./40° C. |
| 3 | 25 mg/mL CBD, Eudragit S100, 5% P188 | 0, 7, 21, 42 | 40° C. 75% RH |
| 4 | 24mg/mL CBD 0.6 mg/mL THC HPMCAS-L | 0, 7, 28 | 5° C./30° C. |

Tests were undertaken at the various time points to determine the following: appearance; cannabinoid assay; differential scanning calorimetry (DSC) and particle size via the dry dispersion method.

In the case of formulation number 4, this formulation contains a mixture of highly purified CBD and CBD BDS. In order to determine the stability of this formulation the concentration of the major cannabinoids in the formulation, namely CBD and THC were determined along with the degradation products.

Tables 9 to 12 below demonstrate the data obtained from the stability study.

TABLE 9

Stability study outcomes of a 30 mg/mL HPMCAS-L Suspension

| | | % of Active | | |
| --- | --- | --- | --- | --- |
| | Timepoint | 5° C. | 25° C. | 30° C. |
| CBD | Initial | 100.0 | 100.0 | 100.0 |
| | 1 week | 97.5 | 98.4 | 97.4 |
| | 3 week | 100.9 | 99.1 | 98.9 |
| | 6 week | 101.5 | 101.8 | 101.0 |
| CBD-C4 | Initial | 0.3 | 0.3 | 0.3 |
| | 1 week | 0.3 | 0.3 | 0.3 |
| | 3 week | 0.3 | 0.3 | 0.3 |
| | 6 week | 0.3 | 0.3 | 0.3 |
| CBDV | Initial | 0.2 | 0.2 | 0.2 |
| | 1 week | 0.3 | 0.3 | 0.3 |
| | 3 week | 0.3 | 0.3 | 0.3 |
| | 6 week | 0.3 | 0.3 | 0.3 |
| RRT 0.54 | Initial | 0.0 | 0.0 | 0.0 |
| | 1 week | 0.0 | 0.1 | 0.0 |
| | 3 week | 0.0 | 0.0 | 0.0 |
| | 6 week | 0.0 | 0.0 | 0.0 |
| RRT 0.52 | Initial | 0.0 | 0.0 | 0.0 |
| | 1 week | 0.0 | 0.0 | 0.0 |
| | 3 week | 0.0 | 0.0 | 0.0 |
| | 6 week | 0.0 | 0.0 | 0.0 |

TABLE 10

Stability study outcomes of a 25 mg/mL CBD S100 with 20% p188 Suspension

|  | Timepoint (weeks) | % of Active 25° C. | % of Active 40° C. |
|---|---|---|---|
| CBD | 0 | 100.00 | 100.00 |
|  | 1 | 102.40 | 97.74 |
|  | 3 | 105.94 | 106.88 |
|  | 6 | 105.64 | 105.15 |
| CBD-C4 | 0 | 0.31 | 0.31 |
|  | 1 | 0.31 | 0.30 |
|  | 3 | 0.33 | 0.33 |
|  | 6 | 0.32 | 0.32 |
| CBDV | 0 | 0.31 | 0.31 |
|  | 1 | 0.33 | 0.31 |
|  | 3 | 0.33 | 0.33 |
|  | 6 | 0.33 | 0.33 |
| THC | 0 | 0 | 0 |
|  | 1 | 0 | 0 |
|  | 3 | 0 | 0 |
|  | 6 | 0 | 0 |

TABLE 11

Stability study outcomes of a 25 mg/mL CBD S100 with 5% p188 Suspension

|  | Timepoint (weeks) | % of Active 40° C. |
|---|---|---|
| CBD | 0 | 100.00 |
|  | 1 | 101.09 |
|  | 3 | 99.35 |
|  | 6 | 100.13 |
| CBD-C4 | 0 | 0.30 |
|  | 1 | 0.29 |
|  | 3 | 0.31 |
|  | 6 | 0.32 |
| CBDV | 0 | 0.32 |
|  | 1 | 0.33 |
|  | 3 | 0.32 |
|  | 6 | 0.33 |
| THC | 0 | 0.00 |
|  | 1 | 0.00 |
|  | 3 | 0.00 |
|  | 6 | <BLQ |
| CBD-C1 | 0 | 0.05 |
|  | 1 | 0.04 |
|  | 3 | 0.05 |
|  | 6 | 0.04 |

TABLE 12

Stability study outcomes of a 24 mg/mL CBD 0.6 mg/mL THC HPMCAS-L Suspension

| Assay | Time point (weeks) | % of Active 5° C. | % of Active 30° C. 65% RH |
|---|---|---|---|
| CBD | Initial | 104.6 | 104.6 |
|  | 2 weeks | 105.8 | 105.3 |
|  | 4 weeks | 106.6 | 106.7 |
| THC | Initial | 99.2 | 99.2 |
|  | 2 weeks | 101.3 | 101.0 |
|  | 4 weeks | 102.0 | 102.2 |
| CBE I | Initial | 0.2 | 0.2 |
|  | 2 weeks | 0.2 | 0.2 |
|  | 4 weeks | 0.2 | 0.2 |
| CBD-C4 | Initial | 0.3 | 0.3 |
|  | 2 weeks | 0.3 | 0.3 |
|  | 4 weeks | 0.3 | 0.3 |
| CBG | Initial | 1.4 | 1.4 |
|  | 2 weeks | 1.4 | 1.4 |
|  | 4 weeks | 1.4 | 1.4 |
| CBN | Initial | 0.1 | 0.1 |
|  | 2 weeks | 0.2 | 0.2 |
|  | 4 weeks | 0.1 | 0.1 |
| CBC | Initial | 2.9 | 2.9 |
|  | 2 weeks | 2.9 | 2.9 |
|  | 4 weeks | 2.9 | 2.9 |
| OH-CBD | Initial | 0.6 | 0.6 |
|  | 2 weeks | 0.6 | 0.6 |
|  | 4 weeks | 0.6 | 0.6 |
| CBDV | Initial | 0.8 | 0.8 |
|  | 2 weeks | 0.8 | 0.8 |
|  | 4 weeks | 0.8 | 0.8 |

The results presented in Tables 9 to 12 demonstrate that over a period of 1 month at the accelerated conditions there are no major increases in the degradants or decreases in the amount of CBD.

In conclusion the formulations comprising microparticles of cannabinoid and a polymer are stable and allow a shelf life of 6 months.

Example 5: Particle Size of an Enteric-Release and a Colonic-Release Microparticulate Formulation The different formulations from the short-term stability study as described in Example 4 above were tested to measure the particle size of the microparticles.

In the case the formulation described in Table 15, this formulation contains a mixture of highly purified CBD and CBD BDS. I Tables 13 to 15 below describe these data.

TABLE 13

Particle size of 30 mg/mL HPMCAS-L Suspension

| Time point (weeks) | $D_{10}$ (μm) 5° C. | $D_{10}$ (μm) 25° C. | $D_{10}$ (μm) 30° C. | $D_{50}$ (μm) 5° C. | $D_{50}$ (μm) 25° C. | $D_{50}$ (μm) 30° C. | $D_{90}$ (μm) 5° C. | $D_{90}$ (μm) 25° C. | $D_{90}$ (μm) 30° C. |
|---|---|---|---|---|---|---|---|---|---|
| 0 | 3.03 | 3.03 | 3.03 | 7.14 | 7.14 | 7.14 | 21.3 | 21.3 | 21.3 |
| 1 | 3.09 | 3.31 | 3.02 | 7.34 | 9.17 | 6.26 | 42.5 | 20.7 | 14.2 |
| 3 | 2.94 | 3.04 | 3.16 | 6.16 | 6.33 | 6.2 | 14.3 | 14.7 | 14.4 |
| 6 | 3.12 | 3.21 | 3.33 | 7.42 | 6.89 | 7.08 | 33.7 | 22.7 | 87.4 |

TABLE 14

Particle size of 25 mg/mL CBD S100 Suspension

| Time point | $D_{10}$ (µm) | | $D_{50}$ (µm) | | $D_{90}$ (µm) | |
|---|---|---|---|---|---|---|
| (weeks) | 25° C. | 40° C. | 25° C. | 40° C. | 25° C. | 40° C. |
| 0 | 3.72 | 3.72 | 9.33 | 9.33 | 20.1 | 20.1 |
| 1 | 3.79 | 4.01 | 9.04 | 10.9 | 21.7 | 48.4 |
| 3 | 3.80 | 3.80 | 8.75 | 9.81 | 18.6 | 36.7 |
| 6 | 3.83 | 3.49 | 8.87 | 9.64 | 18.5 | 23.9 |

TABLE 15

Particle size of 24 mg/mL CBD 0.6 mg/mL THC HPMCAS-L Suspension

| Time point (weeks) | $D_{10}$ (µm) 25° C. | $D_{50}$ (µm) 25° C. | $D_{90}$ (µm) 25° C. |
|---|---|---|---|
| 0 | 4.10 | 11.1 | 29.1 |
| 1 | 4.01 | 10.3 | 24.7 |
| 4 | 3.92 | 10.4 | 26.6 |

As can be seen the particle size of the cannabinoid containing microparticulate formulations did not alter considerably over the course of the stability study meaning that during storage of the formulation there will not be any degradation of the particle size.

Example 6: Bioavailability of a Colonic-Release Microparticulate Formulation In order to determine whether the colonic-release (CR) formulations detailed in Example 1 were able to provide suitable bioavailability a PK study using rats was undertaken.

These formulations were compared with a Type I oil-based formulation.

The active used was CBD for the Type I oil-based formulation and the colonic-release and the enteric-release formulations were tested with two different actives; CBD alone or a combination of THC and CBD.

The design of the study was to measure the plasma pharmacokinetics of CBD and THC and their metabolites (hydroxy-CBD, carboxy CBD, hydroxy-THC and carboxy-THC) following oral administration to the rat.

Male han wistar rats (n=3) per group were fasted prior to dosing and fed at 4 hours post dosing.

The sampling times were: 0, 1, 2, 4, 8, 12 and 24 h post-dose. The determination of CBD, THC and their respective metabolites was performed by protein precipitation with reverse phase liquid chromatography with tandem mass spectrometric detection. The LLOQ of CBD was 1 ng/mL and all metabolites had an LLOQ of 0.5 ng/mL.

The human equivalent dose (HED) can be estimated using the following formula:

$$HED = \text{Animal dose (mg/kg) multiplied by } \frac{\text{Animal } K_m}{\text{Human } K_m}$$

The Km for a rat is 6 and the Km for a human is 37.

Thus, for a human a 10 mg/kg dose in a rat equates to a human dose of about 1.6 mg/kg.

Table 16 details the bioavailability of the different formulations tested and FIG. 1 details the AUC of the non-active metabolite of CBD, 7-COOH CBD. As can be seen in the graph in both the CBD microparticulate suspension and the suspension containing a mixture of highly purified CBD and CBD BDS there is one result which is an outlier suggesting that the actual concentration of 7-COOH CBD was much lower than the mean AUC recorded in the table.

TABLE 16

Estimation of bioavailability (using AUC(0-t) data)

| | Analyte | | | Ratios | | | Analyte | | | Ratios | | |
|---|---|---|---|---|---|---|---|---|---|---|---|---|
| AUC 0-t (H/g/ml/mg) | CBD | OH-CBD | COOH-CBD | CBD | OH-CBD | COOH-CBD | THC | OH-THC | COOH-THC | THC | OH-THC | COOH-THC |
| Type I (oil-based) | 386 | 61.4 | 290 | 1 | 0.16 | 0.75 | | | | | | |
| CR (CBD) | 338 | 53.8 | 146 | 1 | 0.16 | 0.43 | | | | | | |
| CR (pure CBD + CBD BDS) | 187 | 27.6 | 164 | 1 | 0.15 | 0.88 | 1470 | 148 | 218 | 1 | 0.10 | 0.15 |

The results demonstrate a significant decrease in the amount of the inactive carboxy-CBD metabolite in the colonic-release and the enteric-release formulations in comparison to the Type I oil-based formulation. This is very beneficial as it means that a lower dose of the active can be administered to enable the same effect.

Example 7: Long-Term Stability

The suspension containing a mixture of highly purified CBD and CBD BDS in HPMCAS-L was taken forward into a long-term stability study as shown in Table 17. In order to determine the stability of this formulation the concentration of the major cannabinoids in the formulation, namely CBD and THC were determined along with the degradation products.

TABLE 17

Formulation and storage conditions for stability testing

| Formulation with microparticulates containing: | Time points (weeks) | Storage conditions |
|---|---|---|
| 25 mg/mL CBD 0.6 mg/mL THC; HPMCAS-L | 0, 3, 6, 12, 24 | 5° C./25° C./30° C. |

Tests were undertaken at the various time points to determine the following: appearance; cannabinoid assay; and particle size via the dry dispersion method.

Table 18 below demonstrates the data obtained from the stability study.

TABLE 18

Stability study outcomes of a 25 mg/mL CBD 0.6 mg/mL THC HPMCAS-L Suspension

| | | % of Active | | |
|---|---|---|---|---|
| | Timepoint | 5° C. | 25° C. | 30° C. |
| CBD | Initial | 100.0 | 100.0 | 100.0 |
| | 3 week | 100.06 | 101.44 | 101.42 |
| | 6 week | 98.12 | 96.15 | 96.34 |
| | 12 week | 99.96 | 98.56 | 98.96 |
| | 24 week | 99.32 | 98.29 | 97.53 |
| THC | Initial | 100.00 | 100.00 | 100.00 |
| | 3 week | 98.19 | 99.74 | 99.83 |
| | 6 week | 98.36 | 97.93 | 97.50 |
| | 12 week | 100.34 | 99.14 | 99.57 |
| | 24 week | 101.12 | 100.17 | 98.62 |
| CBE I | Initial | 0.30 | 0.31 | 0.30 |
| | 3 week | 0.31 | 0.31 | 0.31 |
| | 6 week | 0.31 | 0.32 | 0.31 |
| | 12 week | 0.30 | 0.30 | 0.30 |
| | 24 week | 0.31 | 0.32 | 0.30 |
| OH-CBD | Initial | 0.55 | 0.56 | 0.55 |
| | 3 week | 0.54 | 0.58 | 0.55 |
| | 6 week | 0.50 | 0.52 | 0.51 |
| | 12 week | 0.56 | 0.58 | 0.56 |
| | 24 week | 0.55 | 0.57 | 0.59 |
| CBN | Initial | 0.12 | 0.12 | 0.12 |
| | 3 week | 0.12 | 0.13 | 0.13 |
| | 6 week | 0.10 | 0.10 | 0.10 |
| | 12 week | 0.13 | 0.13 | 0.13 |
| | 24 week | 0.12 | 0.12 | 0.13 |

The results presented in Table 18 demonstrate that over a period of 6 months at differing temperatures there are no major increases in the degradants (CBE-I, OH-CBD, CBN) or decreases in the amount of the major cannabinoids CBD or THC.

In conclusion the formulations comprising microparticles of cannabinoid and a polymer are stable and allow a shelf life of at least 6 months.

Example 8: Particle Size from Long-Term Study

The formulation from the long-term stability study as described in Example 7 above was tested to measure the particle size of the microparticles.

Table 19 below describes this data.

TABLE 19

Particle size of pure CBD + CBD BDS (25 mg/mL CBD 0.6 mg/mL THC) HPMCAS-L Suspension

| Time point | $D_{10}$ (μm) | | | $D_{50}$ (μm) | | | $D_{90}$ (μm) | | |
|---|---|---|---|---|---|---|---|---|---|
| (weeks) | 5° C. | 25° C. | 30° C. | 5° C. | 25° C. | 30° C. | 5° C. | 25° C. | 30° C. |
| 0 | 3.25 | 3.35 | 3.35 | 7.24 | 7.24 | 7.24 | 17.3 | 17.3 | 17.3 |
| 3 | 3.65 | 3.22 | 3.11 | 8.25 | 6.98 | 6.50 | 18.6 | 16.8 | 15.7 |
| 6 | 3.67 | 3.24 | 3.06 | 8.37 | 6.94 | 6.37 | 18.2 | 17.3 | 15.5 |
| 12 | 3.77 | 3.25 | 3.09 | 8.71 | 6.87 | 6.20 | 19.4 | 18.9 | 14.1 |
| 24 | 3.61 | 3.19 | 3.06 | 7.99 | 6.61 | 6.22 | 17.0 | 15.9 | 15.2 |

As can be seen the particle size of the cannabinoid containing microparticulate formulations did not alter considerably over the course of the stability study meaning that during long-term storage of the formulation there will not be any degradation of the particle size.

The invention claimed is:

1. A microparticulate comprising one or more cannabinoids and a pH dependent release polymer, wherein the one or more cannabinoids are present in an amount ranging from 10% w/w to about 50% w/w, and the pH dependent release polymer is present in an amount ranging from ranging from about 5 w/w to about 85% w/w, wherein the pH dependent release polymer is present as a coating disposed over the one or more cannabinoids, or the one or more cannabinoids are dispersed in a matrix comprising the pH dependent release polymer.

2. The microparticulate of claim 1, wherein the one or more cannabinoids are: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV), tetrahydrocannabivarinic acid (THCVA), or combinations thereof.

3. The microparticulate of claim 1, wherein the one or more cannabinoids comprise CBD, THC, or combinations thereof.

4. The microparticulate of claim 1, wherein the pH dependent release polymer is selected from the group consisting of: a copolymer of methacrylic acid and methacrylate, a copolymer of methacrylic acid and methyl methacrylate (Eudragit), a copolymer of methacrylic acid and ethylacrylate, hydroxypropyl methyl cellulose acetate succinate (HPMCAS), hydroxypropyl methyl cellulose phthalate (HPMCP), polyvinyl acetate phthalate (PVAP), a copolymer of methyl vinyl ether and maleic anhydride, cellulose acetate phthalate (CAP), cellulose acetate butyrate (CAB), cellulose acetate trimellitate (CAT), cellulose acetate succinate (CAS), ethyl cellulose, methyl cellulose, shellac, gellan gum, zein, alginic acid and waxes.

5. The microparticulate of claim 3, wherein the pH dependent release polymer is HPMCAS.

6. The microparticulate of claim 3, wherein the pH dependent release polymer is selected from the group consisting of: HPMCAS-L; HPMCAS-M; and HPMCAS-H.

7. The microparticulate of claim 1, having a particle size ranging from about 1 μm to about 200 μm.

8. The microparticulate of claim 1, having a particle size ranging from about 5 μm to about 100 μm.

9. A unit dose comprising a plurality of the microparticulates of claim 1, further comprising one or more pharmaceutically acceptable excipients.

10. The unit dose of claim 9, wherein the dosage form comprises from 50 mg to about 1000 mg of one or more cannabinoids.

11. The unit dose of claim 9, comprising CBD, wherein after administration of from about 5-25 mg/kg/day, the dosage form provides a steady state $AUC_{0-t}$ ranging from about 170 ng*hr/mL to about 1300 ng*hr/mL.

12. The unit dose of claim 9, comprising CBD, wherein after administration, the dosage form provides a steady state AUC from time zero (t1) to five hours (t2) ($AUC_{t1-t2}$) ranging from 25 ng*hr/mL to 4000 ng*hr/mL AUC.

13. The microparticulate of claim 1, further comprising one or more wetting agents.

14. The microparticulate of claim 13, wherein the one or more wetting agents is a polyoxyethylene-polyoxypropylene block copolymer or sodium carbonate.

15. The unit dose of claim 9, further comprising one or more suspending agents.

16. The unit dose of claim 15, wherein the one or more suspending agents are taken from the group consisting of: polysorbate 20; glycerol; and xanthan gum.

17. The unit dose of claim 9, further comprising one or more pH buffers.

18. The unit dose of claim 17, wherein the one or more pH buffers are citric acid, sodium phosphate dibasic, sodium hydroxide, phosphate buffered saline, or combinations thereof.

19. The unit dose of claim 9, further comprising one or more preservatives.

20. The unit dose of claim 19, wherein the one or more preservatives are potassium sorbate, sodium benzoate, or a combination thereof.

21. The unit dose of claim 9, further comprising one or more antioxidants.

22. The unit dose of claim 21, wherein the one or more antioxidants are butylated hydroxyltoluene, butylated hydroxylanisole, alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, monothioglycerol, or mixtures thereof.

23. The unit dose of claim 9, further comprising one or more solvents.

24. The unit dose of claim 23, wherein the one or more solvents are water; ethanol, acetone, or combinations thereof.

25. The unit dose of claim 9, wherein the unit dose is formulated as a mucoadhesive gel; a tablet; a powder; a liquid gel capsule; a solid capsule; an oral solution; an oral suspension; a granulate; an extrudate; or a sprinkle.

26. A microparticulate comprising CBD and a pH dependent release polymer, wherein the CBD is present in an amount ranging from 10% w/w to about 50% w/w, and the pH dependent release polymer is present in an amount ranging from ranging from about 5% w/w to about 85% w/w,
  wherein the pH dependent release polymer comprises hydroxypropyl methyl cellulose acetate succinate (HPMCAS), and the HPMCAS is present as a coating disposed over the CBD, or the CBD is dispersed in a matrix comprising the HPMCAS.

27. The microparticulate of claim 26, wherein the pH dependent release polymer is HPMCAS-L, HPMCAS-M, or HPMCAS-H.

28. The microparticulate of claim 26, having a particle size ranging from about 5 μm to about 100 μm.

29. The microparticulate of claim 28, when the HPMCAS is disposed over the CBD.

30. The microparticulate of claim 29, wherein the CBD is present in an amount ranging from 10% w/w to about 30% w/w, and the HPMCAS is present in an amount ranging from ranging from about 5% w/w to about 80% w/w.

\* \* \* \* \*